United States Patent [19]
Lavash et al.

[11] Patent Number: 5,860,965
[45] Date of Patent: *Jan. 19, 1999

[54] ABSORBENT ARTICLE HAVING A RELEASABLE ADHESIVE PATCH

[75] Inventors: Bruce William Lavash, West Chester; Charles John Berg, Jr., Cincinnati, both of Ohio

[73] Assignee: The Procter & Gamble Company, Cincinnati, Ohio

[*] Notice: The term of this patent shall not extend beyond the expiration date of Pat. No. 5,281,209.

[21] Appl. No.: 745,990

[22] Filed: Nov. 8, 1996

Related U.S. Application Data

[63] Continuation of Ser. No. 203,722, Feb. 28, 1994, abandoned, which is a continuation of Ser. No. 991,786, Dec. 17, 1992, abandoned, which is a continuation-in-part of Ser. No. 769,891, Oct. 1, 1991, abandoned, and a continuation-in-part of Ser. No. 832,246, Feb. 7, 1992, abandoned, and a continuation-in-part of Ser. No. 906,593, Jun. 30, 1992, Pat. No. 5,281,209, and a continuation-in-part of Ser. No. 42,840, Apr. 5, 1993, Pat. No. 5,354,400, which is a continuation of Ser. No. 769,607, Oct. 1, 1991, abandoned.

[51] Int. Cl.⁶ .................................................. A61F 13/15
[52] U.S. Cl. ........................... 604/390; 604/387; 604/389
[58] Field of Search ................................. 604/358, 385.1, 604/393

[56] References Cited

U.S. PATENT DOCUMENTS

| | | |
|---|---|---|
| D. 327,319 | 6/1992 | Ruffo et al. . |
| 3,245,855 | 4/1966 | Stenvall . |
| 3,397,697 | 8/1968 | Rickard . |
| 3,800,796 | 4/1974 | Jacob .................................. 604/385.2 |
| 3,913,580 | 10/1975 | Ginocchio . |
| 3,926,191 | 12/1975 | Tritsch .................................... 604/390 |
| 3,929,134 | 12/1975 | Karami . |
| 3,943,609 | 3/1976 | Egan, Jr. . |
| 3,967,624 | 7/1976 | Milnamow . |
| 4,166,464 | 9/1979 | Korpman . |
| 4,285,343 | 8/1981 | McNair . |
| 4,299,223 | 11/1981 | Cronkrite . |
| 4,327,732 | 5/1982 | Thinnes . |
| 4,496,359 | 1/1985 | Pigneul . |
| 4,568,344 | 2/1986 | Suzuki et al. ........................... 604/390 |
| 4,589,876 | 5/1986 | Van Tilburg . |
| 4,596,570 | 6/1986 | Jackson et al. . |
| 4,597,759 | 7/1986 | Johnson . |
| 4,605,404 | 8/1986 | Sneider . |

(List continued on next page.)

FOREIGN PATENT DOCUMENTS

| | | |
|---|---|---|
| 76104512 | 8/1987 | China . |
| 79205822 | 4/1989 | China . |
| 79202379 | 5/1989 | China . |
| 0 301 491 A1 | 2/1989 | European Pat. Off. . |
| 0 464 855 A1 | 1/1992 | European Pat. Off. . |
| 0 471 384 A1 | 2/1992 | European Pat. Off. . |
| 0 471 385 A1 | 2/1992 | European Pat. Off. . |
| 0 471 587 A1 | 2/1992 | European Pat. Off. . |
| 0 472 376 A1 | 2/1992 | European Pat. Off. . |
| 0 511 905 A1 | 11/1992 | European Pat. Off. . |
| 1491234 | 4/1969 | Germany . |
| 3319421 | 11/1984 | Germany . |
| 3326026 | 2/1985 | Germany . |
| 2 118 021 | 10/1983 | United Kingdom . |
| 2 151 460 | 7/1985 | United Kingdom . |
| WO 89/02729 | 4/1989 | WIPO . |
| WO 92/17139 | 10/1992 | WIPO . |
| WO 92/18080 | 10/1992 | WIPO . |

*Primary Examiner*—Robert A. Clarke
*Attorney, Agent, or Firm*—Jeffrey V. Bamber; Steven W. Miller; Jacobus C. Rasser

[57] ABSTRACT

An absorbent article having a main body portion, a pair of flaps joined to the main body portion, and an adhesive patch joined to each flap. Each adhesive patch comprises a first half and a second half releasably secured to the first half. The first half has adhesive zones and release zones, and the second half has adhesive zones and release zones which are removably securable to the release zones and adhesive zones of the first half.

23 Claims, 16 Drawing Sheets

U.S. PATENT DOCUMENTS

| | | |
|---|---|---|
| 4,608,047 | 8/1986 | Mattingly . |
| 4,615,696 | 10/1986 | Jackson et al. . |
| 4,654,040 | 3/1987 | Luceri . |
| 4,687,478 | 8/1987 | Van Tilburg . |
| 4,690,680 | 9/1987 | Higgins . |
| 4,701,171 | 10/1987 | Boland et al. . |
| 4,701,174 | 10/1987 | Johnson . |
| 4,701,178 | 10/1987 | Glaug . |
| 4,704,114 | 11/1987 | Wilson et al. . |
| 4,747,846 | 5/1988 | Boland et al. . |
| 4,756,709 | 7/1988 | Stevens . |
| 4,759,754 | 7/1988 | Korpman . |
| 4,787,896 | 11/1988 | Houghton et al. . |
| 4,790,838 | 12/1988 | Pigneul et al. . |
| 4,795,455 | 1/1989 | Luceri et al. . |
| 4,834,739 | 5/1989 | Linker et al. . |
| 4,857,067 | 8/1989 | Wood et al. . |
| 4,900,319 | 2/1990 | Richwine . |
| 4,900,320 | 2/1990 | McCoy . |
| 4,911,701 | 3/1990 | Mavinkurve .............. 604/387 |
| 4,917,697 | 4/1990 | Osborn, III et al. . |
| 4,936,839 | 6/1990 | Molee et al. . |
| 4,940,462 | 7/1990 | Salerno ................... 604/387 |
| 4,944,735 | 7/1990 | Mokry . |
| 4,985,025 | 1/1991 | Lingertat et al. . |
| 5,080,658 | 1/1992 | Igaue et al. . |
| 5,087,254 | 2/1992 | Davis et al. . |
| 5,125,918 | 6/1992 | Seidy . |
| 5,133,705 | 7/1992 | Nakanishi et al. . |
| 5,135,521 | 8/1992 | Luceri et al. . |
| 5,151,091 | 9/1992 | Glaug et al. . |
| 5,154,715 | 10/1992 | Van Iten . |
| 5,281,209 | 1/1994 | Osborn et al. .......... 604/385.1 |
| 5,324,278 | 6/1994 | Visscher et al. ........ 604/385.1 |
| 5,344,416 | 7/1994 | Niihara ................... 604/387 |
| 5,354,400 | 10/1994 | Lavash et al. .......... 604/385.1 |

ABSORBENT ARTICLE HAVING A RELEASABLE ADHESIVE PATCH

This application is a continuation of 08/203,722, filed on Feb. 28, 1994 now abandoned; which application is a continuation of 07/991,786, filed Dec. 17, 1992, now abandoned; which application is a continuation in part of 07/769,891, filed Oct. 1, 1991, now abandoned; a continuation in part if 07/832,246, filed Feb. 7, 1992, now abandoned; a continuation in part of 0/906,593, filed Jun. 30, 1992, now abandoned; a continuation in part of 07/906,629, filed Jun. 30, 1992, now U.S. Pat. No. 5,281,209; and a continuation in part of 08/042,840, filed Apr. 5, 1993 now U.S. Pat. No. 5,354,400; which application is a continuation of 07/769,607, filed Oct. 1, 1991, now abandoned.

FIELD OF THE INVENTION

The present invention relates to disposable absorbent articles, such as sanitary napkins, adult incontinence devices, and the like. Still more particularly, the present invention concerns such disposable absorbent articles having adhesive securement means, e.g., flap adhesives, central pad adhesives, and the like.

BACKGROUND OF THE INVENTION

All manner and variety of absorbent articles configured for the absorption of body fluids such as menses, urine, and feces are, of course, well known. Absorbent articles, particularly sanitary napkins, having wings or flaps are disclosed in the literature and are available in the marketplace.

Generally, the flaps extend laterally from a central absorbent means and are intended to be folded around the edges of the wearer's panties in the crotch region. Thus, the flaps are disposed between the edges of the wearer's panties in the crotch region and the wearer's thighs.

The flaps serve at least two purposes. First, the flaps prevent exudates which otherwise would soil the edges of the wearer's panties from doing such. Second, the flaps help stabilize the napkin from shifting out of place, especially when the flaps are affixed to the underside of the panties.

Sanitary napkins having flaps of various types are disclosed in U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,271, entitled "Sanitary Napkin", which issued to Clark on Apr. 2, 1957. All of the above Patents are incorporated herein by reference.

Commonly, the flaps are provided with an adhesive attachment means, or flap adhesive, for affixing the flaps to the underside of the wearer's panties. The flap adhesive is generally provided with a release liner to protect the adhesive from contaminants such as dirt, keep the adhesive from drying out and keep the adhesive from sticking to the skin of the wearer and/or extraneous surfaces prior to use. The release liner is peeled from the flap adhesive to expose the adhesive surface. The adhesive surface is then applied to the underside of the panties to secure the flap in place. After being peeled from the flap adhesive, the release liner is discarded. However, this arrangement requires the use of two hands to remove the release liner from each flap, i.e., the user must hold the flap with one hand and peel the release liner with the other hand. This also requires the user to dispose of the release liners which have been removed from the flaps of the sanitary napkin. Therefore, there is a need for a sanitary napkin having flaps which can be manipulated and applied using one hand. There is also a need for a sanitary napkin with adhesive attachment means comprising an adhesive patch that can be releasably secured to itself thereby eliminating the need for separate pieces of release paper for the adhesive attachment means.

While flaps greatly improve the effectiveness of a sanitary napkin, the flaps of a sanitary napkin may hinder or impede application of the sanitary napkin to the crotch of the wearer's panty. Currently, each of the flaps of a sanitary napkin have an end, the distal end, which may move freely relative to the sanitary napkin. Once the release paper of the central pad adhesive is removed by the wearer, the distal ends of the flaps may fall between the crotch portion of the wearer's panty and the sanitary napkin and may become adhered to the central pad adhesive. Therefore, there is a need for a sanitary napkin having flaps positioned so that they will not interfere with the application of the sanitary napkin to the panty.

Accordingly, it is an object of the present invention to provide an absorbent article, such as a sanitary napkin, having flaps with an adhesive patch which is releasable from itself and can protect itself from contaminants, drying out, or sticking to extraneous surfaces.

It is also an object of the present invention to provide an absorbent article having flaps with an adhesive patch which eliminates the need for separate pieces of release liner and maintains the flap in a folded configuration until the flap is used.

These and other objects of the present invention will be more readily apparent when considered in reference to the following description and when taken in conjunction with the accompanying drawings.

SUMMARY OF THE INVENTION

In accordance with the present invention, an absorbent article, such as a sanitary napkin, having folded flaps with releasable adhesive patches secured thereto, is provided. The absorbent article comprises a main body portion, a pair of flaps joined to the main body portion, and a self releasable adhesive patch joined to a portion of at least one of the flaps such that a first half of the adhesive patch is superposed by the second half of the adhesive patch when the flap is folded along a fold line. The first half and the second half of the adhesive patch comprise alternating zones of adhesive and release material.

BRIEF DESCRIPTION OF THE DRAWINGS

FIG. 4 is a cross-sectional view of another sanitary napkin embodiment taken from an angle similar to that of FIG. 2a.

DETAILED DESCRIPTION OF PREFERRED EMBODIMENTS

1. Introduction

A. The Absorbent Article In General

Figure 1:
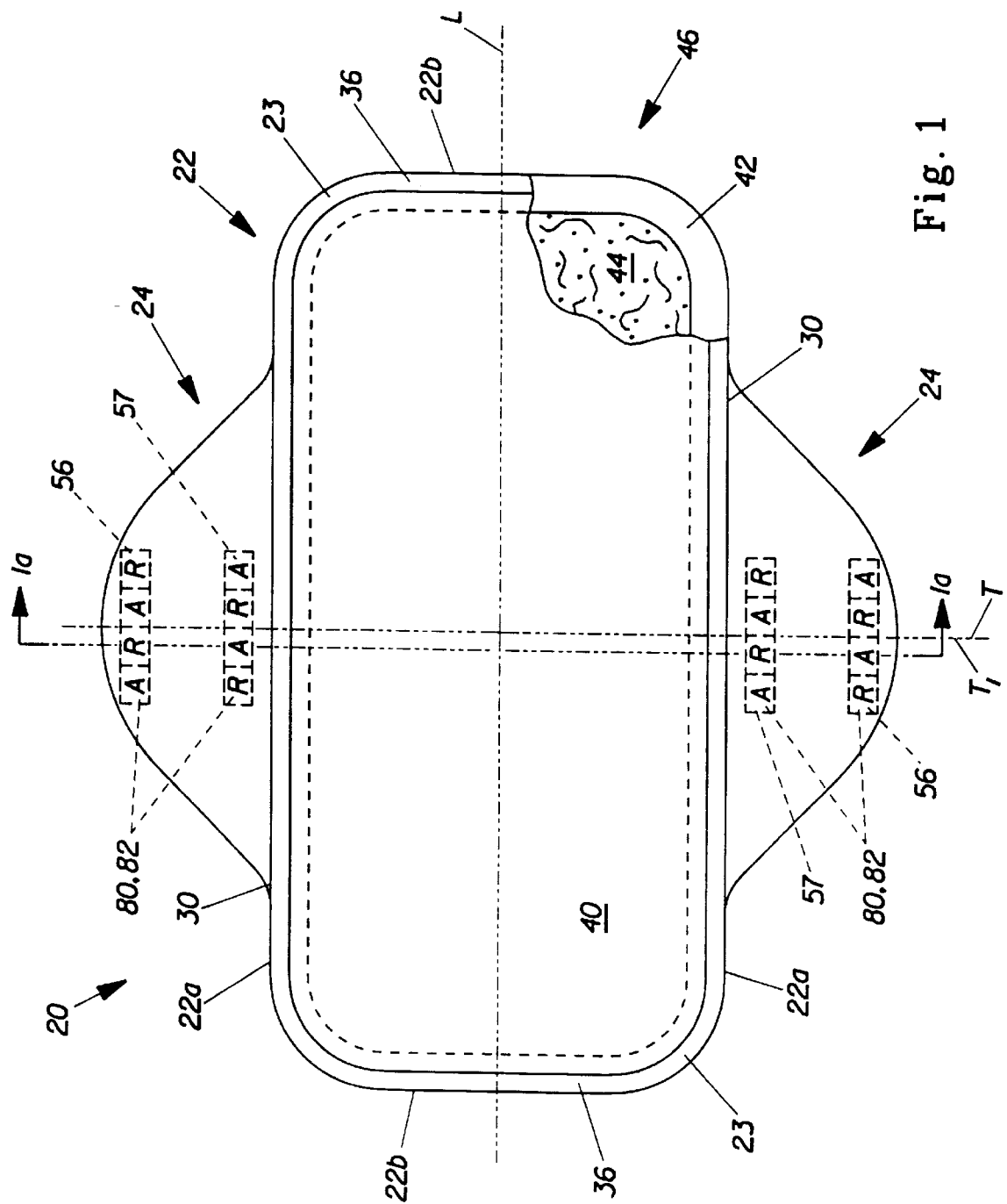
FIG. 1 is a top plan view of a sanitary napkin embodiment of the present invention having portions cut-away to show the absorbent core.

The present invention relates to disposable absorbent articles, such as female sanitary napkins. More particularly, the present invention relates to such disposable absorbent articles having flaps with a flap adhesive which secures the flap to the underside of a user's panty.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, and incontinent pads (and other articles worn in the crotch region of a garment). The term "disposable" refers to articles which are intended to be discarded after a single use and preferably recycled, composted, or otherwise disposed of in an environmentally compatible manner. (That is, they are not intended to be laundered or otherwise restored or reused as an absorbent article.)

The term "sanitary napkin", as used herein, refers to an article which is worn by females adjacent to the pudendal region that is intended to absorb and contain the various exudates which are discharged from the body (e.g., blood, menses, and urine). The present invention, however, is not limited to the particular types or configurations of absorbent articles shown in the drawings.

As used herein, the term "joined" encompasses configurations whereby an element is directly secured to the other element by affixing the element directly to the other element; configurations whereby the element is indirectly secured to the other element by affixing the element to intermediate member(s) which in turn are affixed to the other element; and configurations whereby one element is integral with another element, i.e., one element is essentially part of the other element.

As used herein, the terms "releasable adhesive patch" or "adhesive patch" will refer to an adhesive attachment means comprising adhesive zones and release zones, which adhesive attachment means, after being folded upon itself and secured together, is capable of being released from itself and used as an adhesive attachment means to secure the sanitary napkin (or an element of the sanitary napkin) to the undergarment of the user.

Figure 1A:
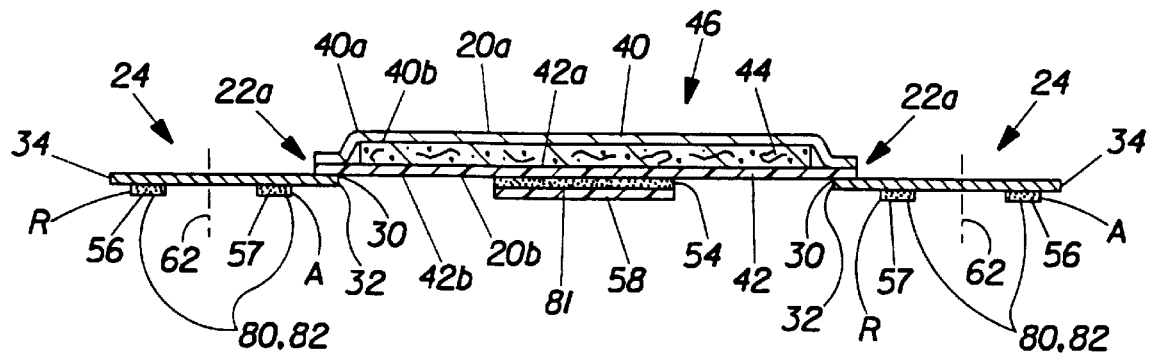
FIG. 1a is a cross-sectional view of the sanitary napkin of FIG. 1 taken along section line a—a.
Figure 1B:
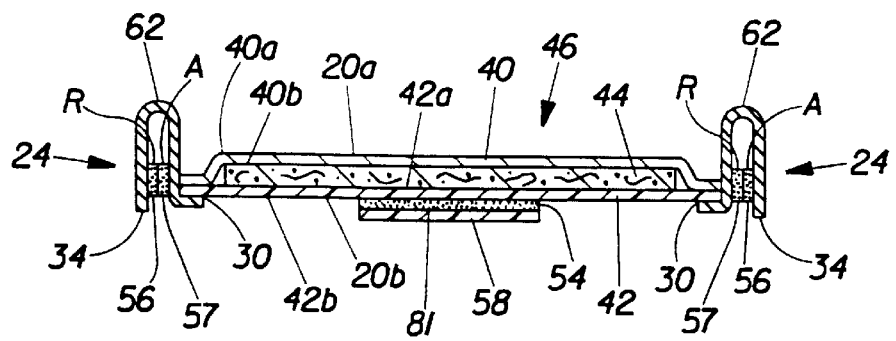
FIG. 1b is a cross-sectional view of the sanitary napkin of FIG. 1a showing the flaps in a folded configuration.

A preferred embodiment of a sanitary napkin 20 of the present invention is shown in FIGS. 1–1b. As shown in FIGS. 1–1b, the sanitary napkin 20 basically comprises a main body portion 22 and two flaps 24 (shown in the extended position) joined to the main body portion 22. Each flap 24 comprises a flap securement member 82. The main body portion 22 comprises an absorbent means represented by an absorbent assembly 46 and a central pad securement member (or simply pad securement member) 81. (In the discussion that follows, unless otherwise noted, the sanitary napkin described herein will have two flaps. While it is not necessary that the napkin have two flaps, two flaps are preferred over one flap. Also, while it is not necessary that the flaps be mirror images of one another, they preferably are. Thus, the description of one flap will be a description of the other, and, for clarity, discussion of the second flap may be omitted.)

The sanitary napkin 20 has two centerlines, a principal longitudinal centerline L and a principal transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

The sanitary napkin 20 is comprised of a topsheet 40, a backsheet 42, an absorbent core 44, and a pair of flaps 24. At least a part of the topsheet 40, backsheet 42, and absorbent core 44 comprise the absorbent assembly 46 of the main body portion 22. The flaps 24 shown in FIGS. 1 and 1a are comprised of discrete pieces of material which are affixed to the main body portion 22. (In alternative embodiments, such as those shown in U.S. Pat. No. 4,917,697 issued to Osborn, the flaps 24 may be integral with the main body portion 22. In such a case, the topsheet 40 may form one surface of both the flaps 24 and the main body portion 22, and the backsheet 42 may form the other surface of the same. In addition, the absorbent material of the sanitary napkin 20 may extend into the flaps 24 to form a flap absorbent core, as described in greater detail in U.S. Pat. No. 4,917,697.) In a particularly preferred embodiment, the main body portion 22 will additionally comprise recessed areas wherein the flaps can be tucked and the flaps will comprise zones of differential extensibility.

2. The Individual Components of the Absorbent Article

The individual components of the sanitary napkin 20 will first be looked at in greater detail.

A. The Topsheet

The topsheet 40 is liquid permeable and when the sanitary napkin 20 is in use, the topsheet 40 is in close proximity to the skin of the user. The topsheet 40 is compliant, soft feeling, and non-irritating to the user's skin. It can be made from any of the materials conventional for this type of use. Nonlimiting examples of suitable materials that can be used as the topsheet 40 are woven and nonwoven polyester, polypropylene, nylon, and rayon and formed thermoplastic films, with formed films being preferred.

Suitable formed films are described in U.S. Pat. No. 3,929,135, entitled "Absorptive Structure Having Tapered Capillaries", which issued to Thompson on Dec. 30, 1975, U.S. Pat. No. 4,324,426, entitled "Disposable Absorbent Article Having A Stain-Resistant Topsheet", which issued to Mullane and Smith on Apr. 13, 1982, U.S. Pat. No. 4,342,314, entitled "Resilient Plastic Web Exhibiting Fiber-Like Properties", which issued to Radel and Thompson on Aug. 3, 1982, and U.S. Pat. No. 4,463,045, entitled "Macroscopically Expanded Three-Dimensional Plastic Web Exhibiting Non-Glossy Visible Surface and Cloth-Like Tactile Impression", which issued to Ahr, Louis, Mullane, and Ouellette on Jul. 31, 1984. Formed films are preferred for the topsheet 40 because they are pervious to liquids and yet non-absorbent. Thus, the surface of the formed film which is in contact with the body remains dry and is more comfortable to the wearer.

The sanitary napkin 20 may also be comprised of components that are extensible (i.e., capable of stretching, particularly in the longitudinal direction) when the sanitary napkin is worn. The sanitary napkin 20 may capable of elongating between about 15% and about 40% of its unstretched length. This extensibility provides better in-use fit, comfort, and decreased staining. In other embodiments, only limited portions of the components of the sanitary napkin 20 are capable of stretching. Such an embodiment (without the releasable adhesive patch of the present invention) is described in greater detail in co-pending, commonly-assigned U.S. patent application Ser. No. 07/769,891, "Absorbent Article Having Flaps and Zones of Differential Extensibility", filed Oct. 1, 1991, in the name of Bruce Lavash, et al.

A particularly preferred topsheet 40 for use in such an embodiment is one which is made in accordance with U.S. Pat. No. 4,463,045 and ring rolled to provide it with a degree of longitudinal extensibility. Suitable processes for ring rolling or "pre-corrugating" are described in U.S. Pat. No. 4,107,364 issued to Sisson on Aug. 15, 1978, U.S. Pat. No. 4,834,741 issued to Sabee on May 30, 1989 and in co-pending, commonly assigned U.S. patent application Ser. No. 07/662,536 entitled "Improved Method And Apparatus For Incrementally Stretching A Zero Strain Stretch Laminate Web To Impart Elasticity Thereto" filed by Gerald M. Weber et al. on Feb. 28, 1991, U.S. patent application Ser. No. 07/662,537 entitled "Improved Method and Apparatus For Incrementally Stretching Zero Strain Stretch Laminate Web In A Non-Uniform Manner To Impart A Varying Degree of Elasticity Thereto" filed by Kenneth B. Buell et al. on Feb. 28, 1991, and U.S. patent application Ser. No. 07/662,543 entitled "Improved Method And Apparatus For Sequentially Stretching Zero Strain Stretch Laminate Web To Impart Elasticity Thereto Without Rupturing The Web" filed by Gerald M. Weber et al. on Feb. 28, 1991. The fold lines in the corrugations of the topsheet should run in the transverse direction so the topsheet is longitudinally extensible.

Such a topsheet is described in greater detail in the following patent applications which were filed on Jun. 23, 1991: U.S. patent application Ser. No. 07/734,404 entitled "Absorbent Articles, Especially Catamenials, Having Improved Fluid Directionality, Comfort and Fit" filed in the names of Thompson, et al.; U.S. patent application Ser. No. 07/734,392 entitled "Fluid Handling Structure for Use in Absorbent Articles" filed in the names of Thompson, et al.; and, U.S. patent application Ser. No. 07/734,405 entitled "Absorbent Core for Use in Catamenial Products" filed in the names of Buenger, et al. These patent applications may be referred to collectively as the "Capillary Channel Fiber" patent applications.

In addition, in preferred embodiments of the present invention, at least a portion of the outer surface 40a of the topsheet 40 is treated with a surfactant. It is preferred that the surfactant be substantially evenly and completely distributed across at least the portion of the outer surface 40a of topsheet 40 that overlays the main body portion 22. This can be accomplished by any of the common techniques well known to those skilled in the art. For example, the surfactant can be applied to topsheet 40 by spraying, by padding, or by the use of transfer rolls.

Treating the outer surface 40a of the topsheet 40 with a surfactant renders the surface of the topsheet 40 more hydrophilic. This results in liquid penetrating the topsheet 40 faster than it would if the surface were not treated. This diminishes the likelihood that menstrual fluids will flow off topsheet 40 rather than being absorbed by the absorbent core 44. Preferably, any portions of the topsheet 40 that overlay the flaps 24 are not treated with the surfactant. This will minimize any tendencies fluids may have to spread laterally across the flaps and to come in contact with the wearer's thighs and other parts of the wearer's body.

In preferred embodiments, the inner surface 40b of the topsheet 40 is secured in contacting relation with the absorbent core 44. This contacting relationship results in liquid penetrating the topsheet 40 faster than if the topsheet 40 were not in contact with the absorbent core 44. The topsheet 40 can be maintained in contact with the absorbent core 44 by applying adhesive to the inner surface 40b of the topsheet 40. Suitable adhesives useful for this purpose are described in U.S. Pat. No. 4,917,697. The adhesives can be applied by the same methods as the surfactant is applied to the outer surface 40a of the topsheet 40.

B. The Absorbent Core

The absorbent core 44 is positioned between the topsheet 40 and the backsheet 42. The absorbent core 44 provides the means for absorbing menstrual fluid. The absorbent core 44 need not have an absorbent capacity much greater than the total amount of menstrual fluid anticipated to be absorbed. The absorbent core 44 is generally compressible, conformable, and non-irritating to the user's skin. It can comprise any material used in the art for such purpose. Examples include comminuted wood pulp which is generally referred to as airfelt, creped cellulose wadding, absorbent foams, absorbent sponges, synthetic staple fibers, polymeric fibers, hydrogel-forming polymer gelling agents, peat moss, or any equivalent material or combinations of materials.

Polymeric gelling agents are those materials which, upon contact with fluids (i.e., liquids) such as water or body fluids, imbibe such fluids and thereby form hydrogels. In this manner, fluids discharged into the absorbent core 44 can be acquired and held by the polymeric gelling agent, thereby providing the articles herein with enhanced absorbent capacity and/or improved fluid retention performance.

The polymeric gelling agent which is employed in the absorbent core 44 will generally comprise particles of a substantially water-insoluble, slightly cross-linked, partially neutralized, hydrogel-forming polymer material. The term "particles", as used herein, can refer to particles in any form, such as in the form of pellets, flakes, or fibers. The characteristics of the absorbent core 44 (including, but not limited to the preferred types of polymer materials used therein, and types of methods which can be used for preparing these polymer particles) are described in greater detail in U.S. Pat. No. 5,009,653 issued to Osborn and the patents incorporated by reference in that patent, the disclosures of which are all incorporated by reference herein.

In one preferred embodiment, the absorbent core 44 is a laminate comprised of a layer of superabsorbent polymer material, such as in the form of particles, disposed between two air-laid tissues, first and second tissue layers (or "upper" and "lower" tissue layers). The first and second tissue layers provide containment of the superabsorbent polymer material, improve lateral wicking of the absorbed exudates throughout the absorbent core 44 and provide a degree of absorbency.

A suitable laminate is the superabsorbent laminate WATER-LOCK L-535 available from the Grain Processing Corporation of Muscatine, Iowa (WATER-LOCK registered TM by Grain Processing Corporation). Such superabsorbent laminates are disclosed in U.S. Pat. No. 4,467,012, entitled "Composition For Absorbent Film And Method Of Preparation", which issued to Pedersen et al. on Aug. 21, 1984, and U.S. Pat. No. 4,260,443, entitled "Laminated Absorbent Process", which issued to Lindsay et al. on Apr. 7, 1981.

The absorbent core 44 may be a laminate, as described above, which is slitted or partially slitted for longitudinal extensibility. This slitted or partially slitted core is described in greater detail in the Capillary Channel Fiber patent applications.

C. The Backsheet

The backsheet 42 is impervious to liquids and, thus, prevents menstrual fluid from soiling the clothing of the user. Any material used in the art for such purpose can be utilized herein. Suitable materials include embossed or non-embossed polyethylene films and laminated tissue. A suitable polyethylene film is manufactured by Monsanto Chemical Corporation and marketed in the trade as Film No. 8020.

In one alternative embodiment of the sanitary napkin 20 (typically in which the topsheet 40 overlays only the main body portion 22 and does not extend out to form the top surface of the flaps), the backsheet 42 may be comprised of two layers. In such a case, the backsheet 42 may comprise a first layer of lofted material disposed on the core-facing side 42a of the backsheet. The purpose of the first layer is to provide a comfortable, non-irritating surface against the body of the wearer. The lofted layer may be comprised of any suitable material, such as a nonwoven material. Preferably, the lofted layer comprises a hydrophobic nonwoven material. The second layer may be disposed on the garment side 42b of the backsheet 42, and may comprise a fluid impervious film. A low density polyethylene material about 0.01 to about 0.05 millimeters in thickness, preferably about 0.02 millimeters in thickness, has been found to work well as this second layer. A polyethylene film, such as is sold by the Monsanto Chemical Corporation and marketed in the trade as Film No. 8020 has been found particularly well suited for this second layer. The backsheet 42 may also be made of a soft, cloth-like material which is hydrophobic relative to the topsheet 40. A polyester or polyolefinic fiber backsheet 42 has been found to work well. A particularly preferred soft, cloth-like backsheet 42 material is a laminate of a polyester nonwoven material and a film such as described in U.S. Pat. 4,476,180 issued to Wnuk on Oct. 9, 1984.

A particularly preferred extensible backsheet 42 is an extended adhesive film Formula #198-338 manufactured by the Findley Adhesives Company of Wauwatosa, Wis. which is described in greater detail in the Capillary Channel Fiber patent applications.

3. Assembly of Components into a Sanitary Napkin and Formation of the Flaps

A. Assembly of Components

As shown in FIGS. 1 and 1a, the topsheet 40 is secured to backsheet 42 along a first seam, such as seam 36. The seam 36 can be formed by any means commonly used in the art for this purpose such as by gluing, crimping, or heat-sealing. The seam 36 is illustrated in FIG. 1 as extending completely around the periphery 23 of the absorbent assembly 46 of the main body portion 22. This is a preferred embodiment for ease of construction. (Other means of uniting the various elements can be used.)

The absorbent assembly 46 is the portion of the main body portion 22 that contains an absorbent means, such as absorbent core 44. The absorbent assembly 46 of the main body portion 22 has a liquid pervious body contacting surface (represented in FIG. 1a by topsheet 40) and an opposed liquid impervious surface (represented in FIG. 1a by backsheet 42). It is to be understood that the embodiment illustrated is only one possible embodiment, albeit a preferred one. Other possible embodiments include one in which an absorbent core 44 is essentially completely wrapped with topsheet before it is placed on a backsheet. The absorbent assembly 46 of the main body portion 22 can also comprise an absorbent core which possesses sufficient integrity to stand alone and is liquid pervious on one surface while the other surface has been treated to render it liquid impervious.

The absorbent assembly 46 of the main body portion 22 may be relatively thick or relatively narrow and thin. A narrow absorbent assembly 46 may be effective because the overall configuration and use of sanitary napkin 20 results in absorbent assembly 46 of the main body portion 22 being maintained in close proximity to the body. Such proximity of the absorbent assembly 46 places it precisely where it should be: very near the body at the vaginal opening. The absorbent assembly 46 of the main body portion 22 can then absorb the vast majority of the menstrual fluid (menses) before it has an opportunity to flow along the sides of the main body portion 22. A thin absorbent assembly may also be desired because it is typically comfortable to the user.

FIGS. 1 and 1a also show the pad securement member 81, central pad adhesive 54, and the flap securement member 82, releasable adhesive patch 80, which are adapted to secure the sanitary napkin 20 to the crotch region of an undergarment.

Although the pad securement member 81 is described herein as a central pad adhesive 54, it should be understood that fastening means other than adhesives can be used as the pad securement member 81. Any type of fastener or combination of fasteners used in the art can be used for such a purpose. For example, the sanitary napkin 20 could be secured to the wearer's undergarment by the fastener described in U.S. Pat. No. 4,946,527 entitled "Pressure-Sensitive Adhesive Fastener and Method of Making the Same" issued to Battrell on Aug. 7, 1990. Other examples of fastening means would include mechanical fasteners such as those which are well known in the art. Particularly preferred mechanical fasteners are disclosed in commonly-assigned, co-pending, U.S. patent application Ser. No. 07/718,727, "Screen Printing Method for Manufacturing a Refastenable Mechanical Fastening System and Fastening System Produced Therefrom", filed Jun. 21, 1991, in the name of Dennis A. Thomas and David J. K. Goulait, and commonly-assigned, co-pending, U.S. patent application Ser. No. 07/719,211, "Method for Manufacturing a Refastenable Mechanical Fastening System having azimuthally angled Prongs and Fastening System Produced Therefrom", filed Jun. 21, 1991, in the name of Dennis A. Thomas and David J. K. Goulait, which patent applications are incorporated herein by reference. Particularly preferred mechanical fasteners for use with absorbent articles such as sanitary napkins are disclosed in U.S. patent application Ser. No. 07/988,541, P&G Case No. 4786, entitled "Disposable Absorbent Article Having An Improved Mechanical Fastening System", filed Dec. 10, 1992, in the names of David J. K. Goulait, Dennis A. Thomas, and Maureen E. Stanley, and U.S. patent application Ser. No. 07/988,636, P&G Case 4785, entitled "Non-Abrasive Mechanical Fastening System and Process of Manufacture Therefor", filed Dec. 10, 1992, in the names of David J. K. Goulait and Dennis A. Thomas, which patent applications are incorporated herein by reference. Additionally, the releasable adhesive patch 80 described herein may also be used as the pad securement member 81. For simplicity, however, the pad securement member 81 will be described in terms of a conventional adhesive attachment means, i.e., central pad adhesive 54.

The central pad adhesive 54 provides an adhesive attachment means for securing main body portion 22 in the crotch portion of a panty. Suitable adhesive fasteners are described in greater detail in U.S. Pat. No. 4,917,697. The adhesive attachment means are respectively covered by removable release liners, central pad release liner 58a and flap release liner 58b. The pressure-sensitive adhesives should be covered with release liners to protect the adhesives from dirt, to keep the adhesives from drying out, and to keep the adhesives from sticking to extraneous surfaces prior to use. Suitable release liners are described in U.S. Pat. No. 4,917,697.

The flap securement member 82 is used to assist in maintaining the flap 24 in position after it is wrapped around the edge of the crotch portion of the panty as described below. The flaps 24 can be maintained in position by attaching the flaps 24 to the undergarment, or to the opposing flap.

While a preferred sanitary napkin embodiment of the present invention has been described, numerous other sanitary napkin embodiments having flaps are available and are disclosed in the literature. These could be provided with the releasable adhesive patch 80 of the present invention. In particular, sanitary napkins having flaps are disclosed in U.S. patent application Ser. No. 07/707,233 entitled "Sanitary Napkin Having Laterally Extensible Means for Attachment to the Undergarment of the Wearer", filed May 21, 1991 in the name of Osborn, et al.; U.S. Pat. Nos. 5,009,653 and 4,950,264, both entitled "Thin, Flexible Sanitary Napkin" which issued to Osborn on Apr. 23, 1991 and Aug. 21, 1990, respectively, U.S. Pat. No. 4,940,462, entitled "Sanitary Napkin With Expandable Flaps" which issued to Salerno on Jul. 10, 1990, U.S. Pat. No. 4,917,697 entitled "Sanitary Napkin Having Flaps and Stress Relief Means" which issued to Osborn, III, et al. on Apr. 17, 1990, U.S. Pat. No. 4,911,701, entitled "Sanitary Napkin Having Elastic Shaping Means" which issued to Mavinkurve on Mar. 27, 1990, U.S. Pat. No. 4,900,320, entitled "Sanitary Napkin With Panty Gathering Flaps" which issued to McCoy on Feb. 13, 1990, U.S. Pat. No. 4,687,478, entitled "Shaped Sanitary Napkin With Flaps", which issued to Van Tilburg on Aug. 18, 1987, U.S. Pat. No. 4,608,047,entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,241, entitled "Sanitary Napkin", which issued to Clark on Apr. 2, 1957. All of the above Patent Applications and Patents are incorporated herein by reference.

Suitable absorbent articles in the form of pantiliners are disclosed in U.S. Pat. No. 4,738,676 entitled "Pantiliner" issued to Osborn on Apr. 19, 1988. Suitable absorbent articles, at least some of which are in the form of adult incontinence products, are described in U.S. patent application Ser. No. 07/637,571 entitled "Absorbent Article Having Rapid Acquiring Wrapped Multiple Layer Absorbent Body" filed by Barry R. Feist, et al. on Jan. 3, 1991.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

B. Construction of the Flaps

The characteristics of the flaps 24 will now be looked at in greater detail. The general construction of flaps 24 suitable for use in the present invention (without the releasable adhesive patch 80 of the present invention) is described in greater detail in the patents incorporated by reference herein, such as U.S. Pat. No. 4,917,697 issued to Osborn; U.S. patent application Ser. No. 07/769,891, "Absorbent Article Having Flaps and Zones of Differential Extensibility", filed Oct. 1, 1991 in the name of Bruce Lavash, et al.; and U.S. patent application Ser. No. 07/832,246, "Absorbent Article Having Inwardly-Folded Pleated Flaps", filed Feb. 7, 1992 in the name of Kaoru Niihara and Thomas W. Osborn, III.

The overall size of the flaps 24 can be readily selected by those skilled in the art. Preferably, the flaps 24 are sized so that the sanitary napkin 20 is from about 10 to about 23 centimeters wide between the distal edges 34 of the flaps at their greatest separation. Preferably each flap 24 is from about 5 to at least about 19 centimeters long in the direction parallel to the principal longitudinal centerline L of the sanitary napkin. However, the flaps 24 may be as small as 0.5 centimeters long in the direction parallel to the principle longitudinal centerline L.

The shape of the flaps 24 can be selected by those skilled in the art. Preferably, not only are the flaps 24 mirror images of each other, the two halves of each flap 26 and 28 are also symmetrical about the flap transverse centerline $T_1$. (It should be understood that the shape and orientation of the flaps described herein are those of a preferred embodiment. They are not mandatory design features.)

Figure 3:
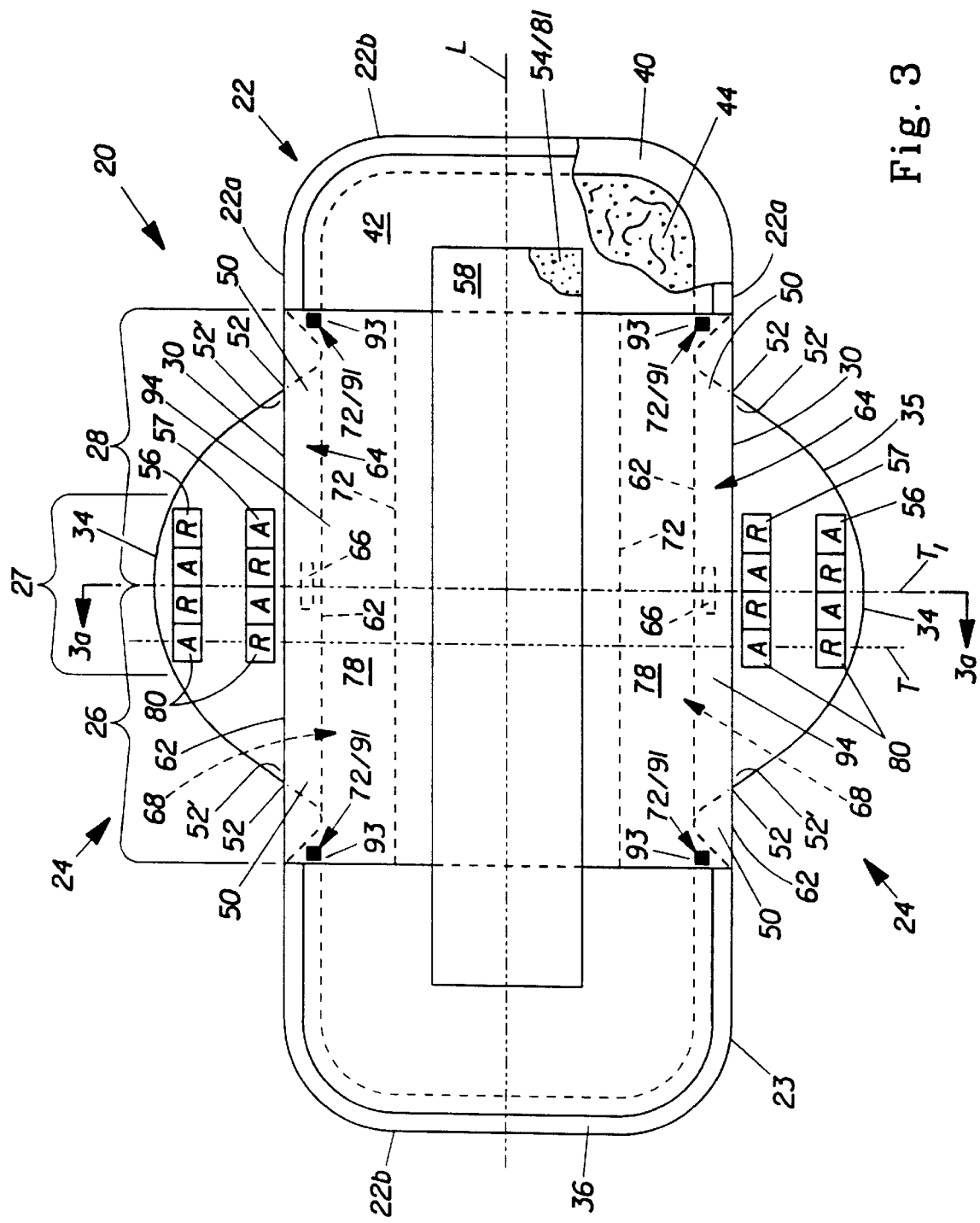
FIG. 3 is a top plan view of an alternate sanitary napkin embodiment of the present invention.

Preferably, as in the sanitary napkin 20 illustrated in FIG. 3, the flaps 24 are positioned slightly forward of the principal transverse centerline T of the sanitary napkin. (In such a case, the flap transverse centerline $T_1$ does not coincide with the principal transverse centerline T of the sanitary napkin 20.) The flaps 24, however, are preferably evenly spaced from the principal longitudinal centerline L of the sanitary napkin.

In a preferred embodiment, the flaps 24 are joined with the main body portion 22 along lines of juncture 30. The lines of juncture can be concave, straight, or convex relative to the principal longitudinal centerline L. The lines of juncture 30 may comprise those lines or areas where separate flap elements are joined to the main body portion 24. Alternatively, when the flaps 24 are integral with the main body portion 22, the lines of juncture 30 may represent lines of demarcation between the main body portion 22 and the flaps 24 (although it is not necessary that there be a precise line of demarcation).

The flaps 24 can be joined with the main body portion 22 in a number of different manners. Many of the different ways a component (such as the flaps 24) can be "joined to" or "associated with", etc. another component, are set forth in the definitions of these terms contained in U.S. Pat. No. 5,007,906 entitled "Decoupled Sanitary Napkin" which issued to Osborn, et al. on Apr. 16, 1991. When the flaps comprise separate elements, they can be joined to the main body portion 22 by any techniques known to those skilled in the art. Such techniques include, but are not limited to adhesives, heat and/or pressure, ultrasonics, etc.

It is not necessary that the flaps 24 extend from (or be joined along) the longitudinal edges 22a of the main body portion 22. The flaps 24 can joined inward (or "inboard") from the longitudinal edges 22a toward the longitudinal centerline such as is shown in U.S. Pat. No. 4,900,320 issued to McCoy on Feb. 13, 1990. The flaps 24 can, thus, each be joined to the main body portion 22 along the principal longitudinal centerline L, or along the longitudinal edges 22a of the main body portion 22, or at any place between the principal longitudinal centerline L and the longitudinal edges 22a of the main body portion 22. The flaps 24 will, of course, generally be on opposite sides of the principal longitudinal centerline L.

C. Releasable Adhesive Patch

1. Releasable Adhesive Patch in General

FIGS. 1, 1a and 1b show a preferred embodiment of a sanitary napkin of the present invention. The sanitary napkin 20 of the present invention comprises at least one releasable adhesive patch 80. Preferably, as shown in FIG. 1, the sanitary napkin 20 has two releasable adhesive patches 80, one for the flap securement member 82 of each flap 24.

The overall size and shape of the releasable adhesive patch 80 can be readily selected by those skilled in the art. Preferably, the releasable adhesive patch 80 is sized and shaped so that it will provide a secure attachment of the flap 24 to the undergarment. However, it should be understood that the size, shape, and orientation of the releasable adhesive patch 80 described herein are those of a preferred embodiment. They are not mandatory design features. For example, each flap 24 could comprise a releasable adhesive patch 80 which is positioned closer to the distal edge 34 of the flap 24 or which is positioned closer to the proximal edge 32 of the flaps.

The releasable adhesive patch 80 will be any patch of material that will adhere to itself with sufficient tenacity to remain in place prior to use, but should be readily removable when the flap 24 is ready to be used. The releasable adhesive patch 80 should also protect itself from contaminants, from drying out, and from sticking to the skin of the wearer and/or extraneous surfaces prior to use. Additionally, the releasable adhesive patch 80 is preferably flexible so as not to inhibit the flexibility of the flap 24.

Referring to FIGS. 1 and 1a, each of the flaps 24 comprises a releasable adhesive patch comprising a first half 56 and a second half 57. The first half 56 is positioned adjacent to the distal edge 34 of the flap 24 and the second half 57 is positioned adjacent the proximal edge 32 of the flap 24. The second half 57 is positioned such that it superposes the first half 56 when the flap 24 is folded along a longitudinally extending fold line 62 as shown in FIG. 1b.

The releasable adhesive patch 80 is shown in FIGS. 1 and 1a as comprising a first half 56 which is discrete from the second half 57. It should be understood that the first half 56 and second half 57 of the releasable adhesive patch 80 may be integral with each other. Additionally, although the first half 56 and the second half 57 are shown in FIG. 1 as having a fold line 62 oriented parallel to the longitudinal centerline L, the first half 56 and the second half 57 may have a fold line oriented parallel to the transverse centerline T or oriented in any other desired direction.

Although the first half 56 is shown positioned substantially adjacent to the distal edge 34 of the flap 24 in FIG. 1, the first half 56 may be positioned closer to the proximal edge 32 of the flap 24, or anywhere between the distal edge 34 and the proximal edge 32. Preferably, the first half 56 will be positioned about 2 mm to about 10 mm from the distal edge 34 of the flap 24 to provide the user with a graspable tab.

Additionally, although the second half 57 is positioned on the flap 24 adjacent the proximal edge 32, the second half 57 may be positioned on a portion of the main body portion 22. However, it is preferred that the first half 56 and second half 57 be positioned on the flap 24. It is also possible for each flap 24 to have more than one releasable adhesive patch 80. However, a single adhesive patch 80 for each flap 24 is preferred.

When the user of the sanitary napkin 20 wishes to expose the adhesive patch 80 and secure the flap 24 to the underside of the user's undergarment, the user simply pulls the distal edge 34 of the flap 24 thereby unfolding the flap 24 from its folded configuration and simultaneously peeling the first half 56 from the second half 57. Preferably, the act of unfolding the flap 24 from its folded configuration and simultaneously peeling the first half 56 from the second half 57, can be accomplished using one hand.

2. Adhesive Patch Comprising Alternating Zones of Adhesive and Release Material

Figure 8:
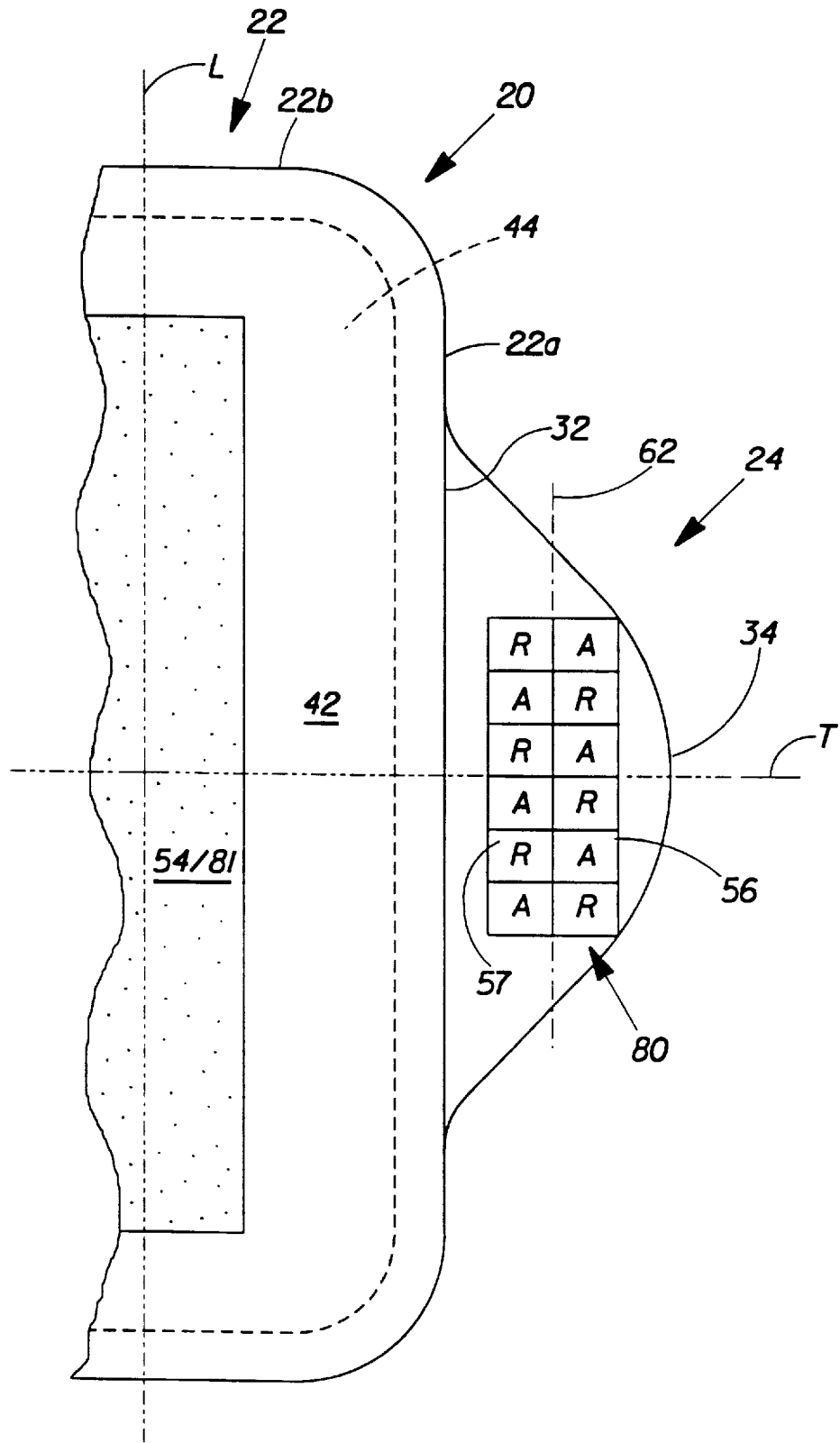
FIG. 8 is a partial top plan view of an alternate sanitary napkin embodiment of the present invention.

The releasable adhesive patch 80 may also comprise alternating zones of adhesive and release material. Referring to FIG. 8, there is shown a portion of a sanitary napkin similar to the sanitary napkin of FIG. 1. The flap 24 of the sanitary napkin 20 of FIG. 8, comprises a releasable adhesive patch 80 having a first half 56 and a second half 57. The first half 56 comprises alternating adhesive zones A and release zones R. The second half 57 also comprises alternating adhesive zones A and release zones R. The alternating adhesive zones A and release zones R of the second half 57 are complementary with the adhesives zones A and release zones R for the first half 56, i.e., the second half 57 has a release zone for each adhesive zone of the first half 56, and the second half 57 has an adhesive zone A for each release zone R of the first half 56.

The adhesive zones A provide an adhesive attachment means for securing the flap 24 in position after it is wrapped around the edge of the crotch portion of the panty as described below. Suitable adhesives for forming the adhesive zones A are described in greater detail in U.S. Pat. No. 4,917,697.

The release zones R provide a release means for the adhesive zones A. The release zones R preferably comprise a release material that is joined to a portion of the wing 24, and may be formed in several different ways. For example, the release zones R may be formed by securing any commercially available release liner to a portion of the flap 24. An example of a suitable release liner is a polyethylene film, the adhesive contacting side of which has been silicone treated to provide easy release from the adhesive zone A. Other examples of suitable release liners are BL 30 MG-A SILOX E1/0 and BL 30 MG-A SILOX 4 P/O both of which are manufactured by the Akrosil Corporation. The release zone can be joined to the flap 24 by any of the techniques known to those skilled in the art. Such techniques include but are not limited to adhesives, heat and/or pressure, ultrasonics, etc.

The release zone R may also comprise a portion of the flap 24 which consists entirely or partially of a material which can act as a suitable release member. Examples of materials which can act as suitable release members and which can be used to form the release zones R, would include woven and nonwoven polyester, polypropylene, nylon, polyethylene, and plastic films, which have been treated with a silicone such as SILOX E1/0, SILOX 4 P/O, SILOX H1A/O, and SILOX H2A/O, all of which are manufactured by the Akrosil Corporation of Menasha, Wis.

Preferably, the release zone R is formed by treating (e.g., coating, painting, spraying, impregnating, etc.) portions of the flap 24 with a substance, such as silicone, so that the treated portion of the flap 24 will function as suitable release zones R. Suitable substances for treating portions of the flap 24 would include a silicone such as SILOX E1/0, SILOX 4 P/O, SILOX H1A/O, and SILOX H2A/O, all of which are manufactured by the Akrosil Corporation. More preferably, the release zones R are formed by spray coating portions of the flap 24 with SILOX H2A/O. Additionally, a silicone compound may be cross-linked or reacted to the surface to imbolize the release material.

Referring to the releasable adhesive patch 80 of one of the flaps 24, the release zones R of the second half 57 are positioned on the flap 24 such that the adhesive zones A of the first half 56 will overlie the release zones R of the second half 57 when the flap 24 is in a folded configuration. Likewise, the release zones R of the first half 56 are positioned on the flap 24 such that the adhesive zones A of the second half 57 will overlie the release zones R of the first half 56 when the flap 24 is in a folded configuration. The release zones R will protect the adhesive zones A from dirt, from drying out, and from sticking to extraneous surfaces. The contact between the release zones R and the adhesive zones A of the releasable adhesive patch 80, also maintains the flap 24 in a folded configuration until the flap is ready to be used.

Although the first half 56 is shown in FIG. 8 as being substantially adjacent to the second half 57, the first half 56 and the second half 57 may be positioned further away from each other. Additionally, although the first half 56 is positioned on the flap 24 adjacent the distal edge 34, the first half 56 may be positioned closer to the proximal edge 32 of the flap 24 or anywhere between the distal edge 34 and the proximal edge 32. However, it is preferred that the first half 56 be positioned 2 mm–10 mm from the distal edge 34 to provide a graspable portion for the user.

It should also be understood that although the fold line 62 between the first half 56 and the second half 57 is oriented parallel to the longitudinal centerline L, the fold line 62 may be oriented parallel to the transverse centerline T or at any other angle relative to the sanitary napkin 20.

Figure 9:
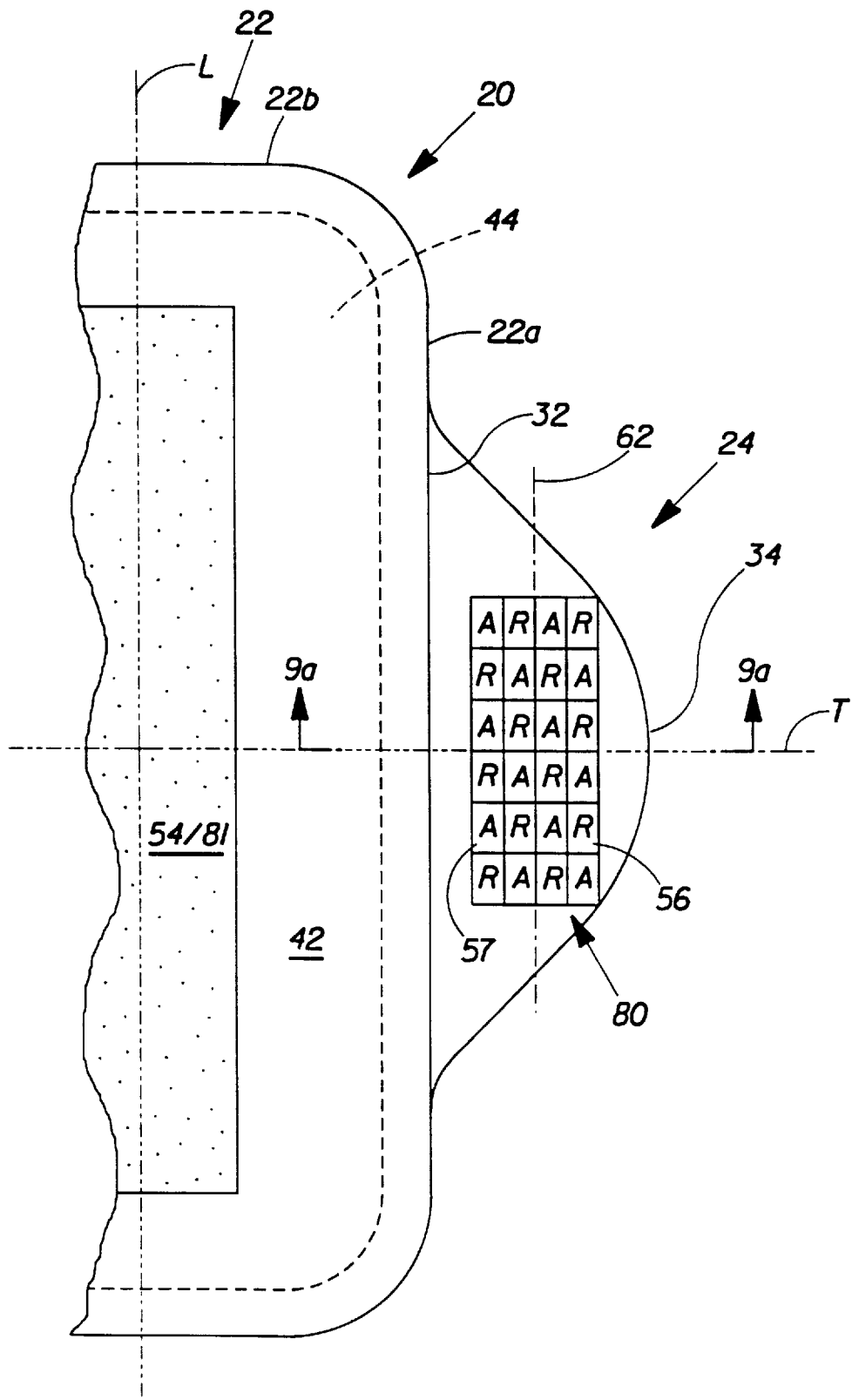
FIG. 9 is a partial top plan view of an alternate sanitary napkin embodiment of the present invention.

Referring to FIG. 9, there is shown a portion of a sanitary napkin substantially the same as the sanitary napkin shown in FIG. 8. However, the first half 56 and the second half 57 of the releasable adhesive patch 30, each comprise two rows of alternating adhesive zones A and release zones R. The adhesive zones A and release zones R of the second half 57 are oriented and arranged such that they will overlay the release zones R and adhesive zones A, respectively, of the first half 56 when the flap 24 is folded along fold line 62.

Figure 9A:
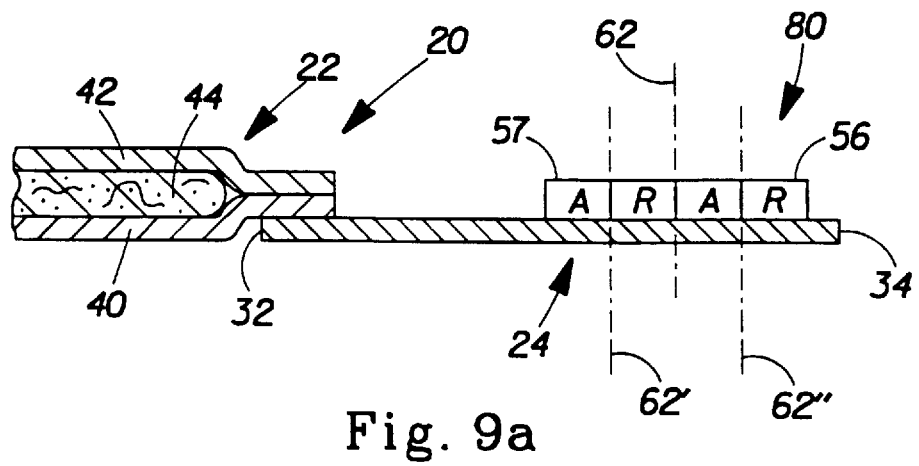
FIGS. 9a–9d are transverse cross-sectional views of the alternate sanitary napkin embodiment of FIG. 9 with the flaps arranged in different fold configurations.
Figure 9B:
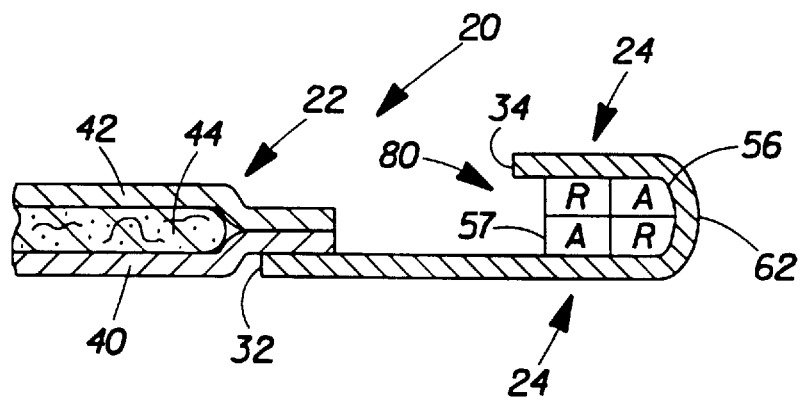
Figure 9C:
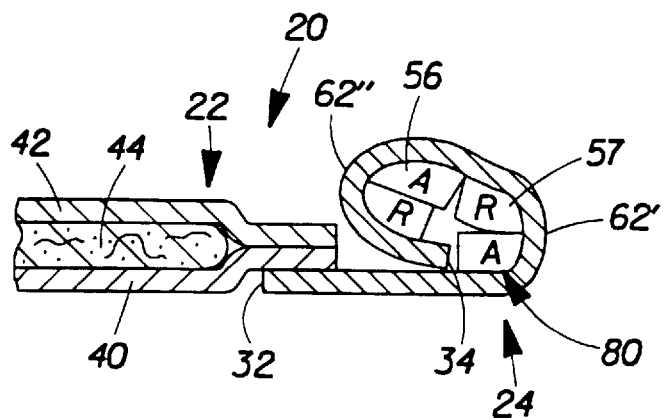
Figure 9D:
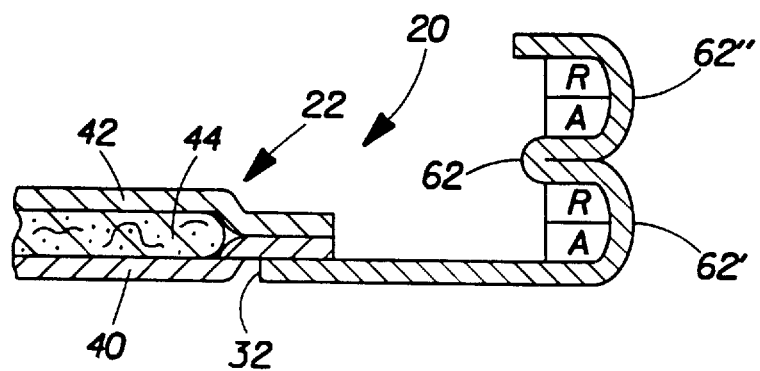

Although the flap 24 of FIG. 9 is shown as comprising only one fold line 62, it is contemplated that a flap 24 may be provided with two or more fold lines. Referring to FIG. 9a there is shown a transverse cross sectional view of the flap 24 of FIG. 9. FIG. 9b is the same transverse cross sectional view shown in FIG. 9a with the exception that the flap 24 is folded along fold line 62. (FIG. 9a additionally shows alternate fold lines 62' and 62".) FIG. 9c shows a transverse cross sectional view of the sanitary napkin 20 of FIG. 3a with the exception that the flap is folded along two fold lines, alternate fold lines 62' and 62". FIG. 9d shows the sanitary napkin of FIG. 9c with the flap additionally folded along fold line 62 to form three separate folds.

Alternate Embodiments

Although both halves of the releasable adhesive patch 80 are shown in FIGS. 1–1b as being joined to a portion of the flap 24, it is not necessary that both halves, 56 and 57, be secured to a portion of the flap 24. The second half 57 may be joined to the flap 24, main body portion 22, or any other portion of the sanitary napkin 20. It is also possible for the central pad adhesive 54 to comprise a releasable adhesive patch 80 such as that described above with respect to the flaps 24.

Figure 7:
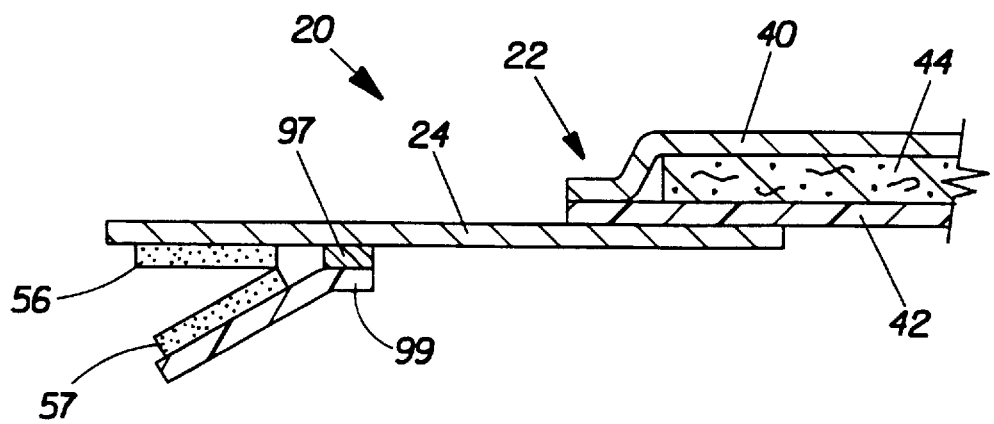
FIG. 7 is a transverse cross-sectional view of a portion of an alternate embodiment of the present invention, showing one of the flaps and part of the main body portion.

In an alternate embodiment, the second half 57 of the releasable adhesive patch 80 may be removably secure to the first half 56 without the flap 24 being folded onto itself or the main body portion 22. FIG. 7 is a transverse cross-sectional view of a portion of a sanitary napkin 20 showing one of the flaps 24 and a portion of the main body portion 22. In this embodiment, the second half 57 of the releasable adhesive patch 80 is hingedly joined to the flap 24. Second half 57 is secured to hinge member 99 which is secured to the flap 24 at bond area 97. When the second half 57 is peeled from the first half 56, it remains joined to the flap 24 at the bond area 97. The bond area 97 may be a single discrete spot bond, group of spot bonds, a solid line of bonding or a segmented line of bonding. The bond area 97 may be located laterally inboard or outboard, or longitudinally forward or behind the flap adhesive 56. The hinge member 99 may be any flexible material. Preferably, the hinge member 99 is made of materials commonly used in the manufacture of disposable absorbent articles such as polymeric nonwovens or films.

Figure 7A:
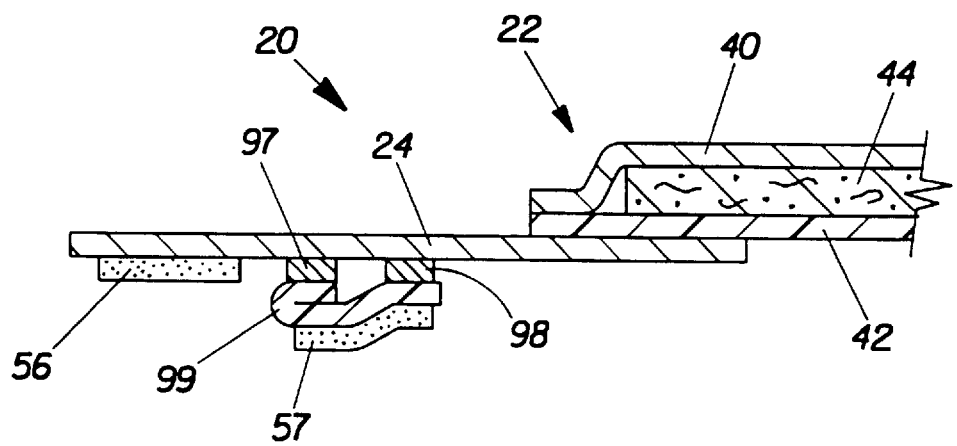
FIG. 7a is a transverse cross-sectional view of a portion of another alternate embodiment of the present invention, showing one of the flaps and part of the main body portion.

A further alternate embodiment is shown in FIG. 7a. After peeling the second half 57 from the first half 56, the user would reattach the loose end of the hinge member 99 to the flap 24 with a bonding material 98. This prevents the loose end of the hinge member 99 from moving freely and potentially interfering with the application of the flap 24. The bonding material 98 could be originally located on either the back of the hinge member 99, on the flap 24 or the main body portion 22. The bonding material 98 could also be a cohesive material, such as a complementary cohesive adhesive, originally located on both the hinge member 99 and the flap 24 or the hinge member 99 and the main body portion 22. As used herein, the term "complementary cohesive adhesive" will refer to an adhesive which will adhere to the same or similar adhesive but not to other surfaces.

Figure 5:
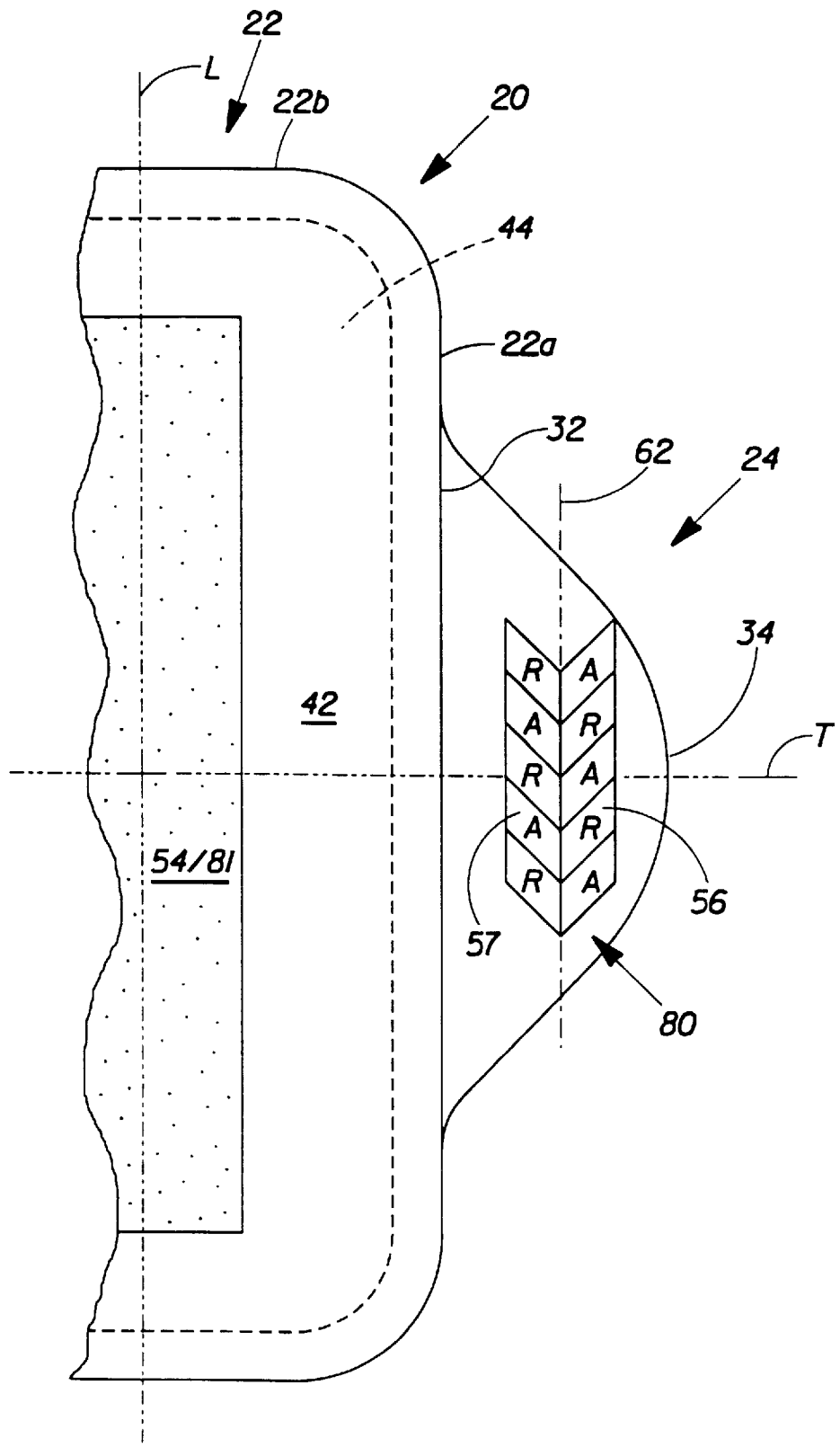
FIG. 5 is a partial top plan view of an alternate sanitary napkin embodiment of the present invention.
Figure 5A:
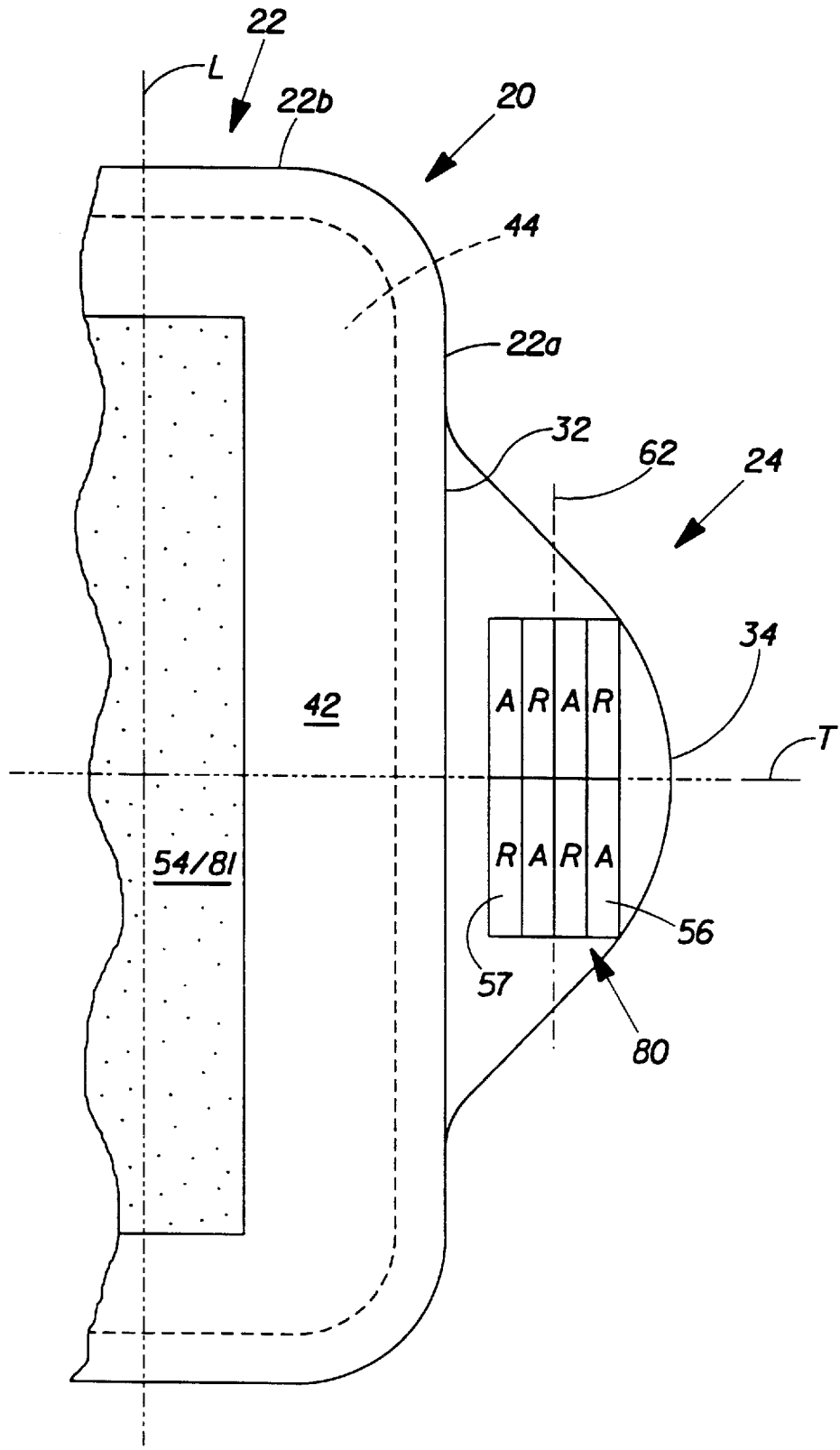
FIG. 5a is a partial top plan view of an alternate sanitary napkin embodiment of the present invention.
Figure 5B:
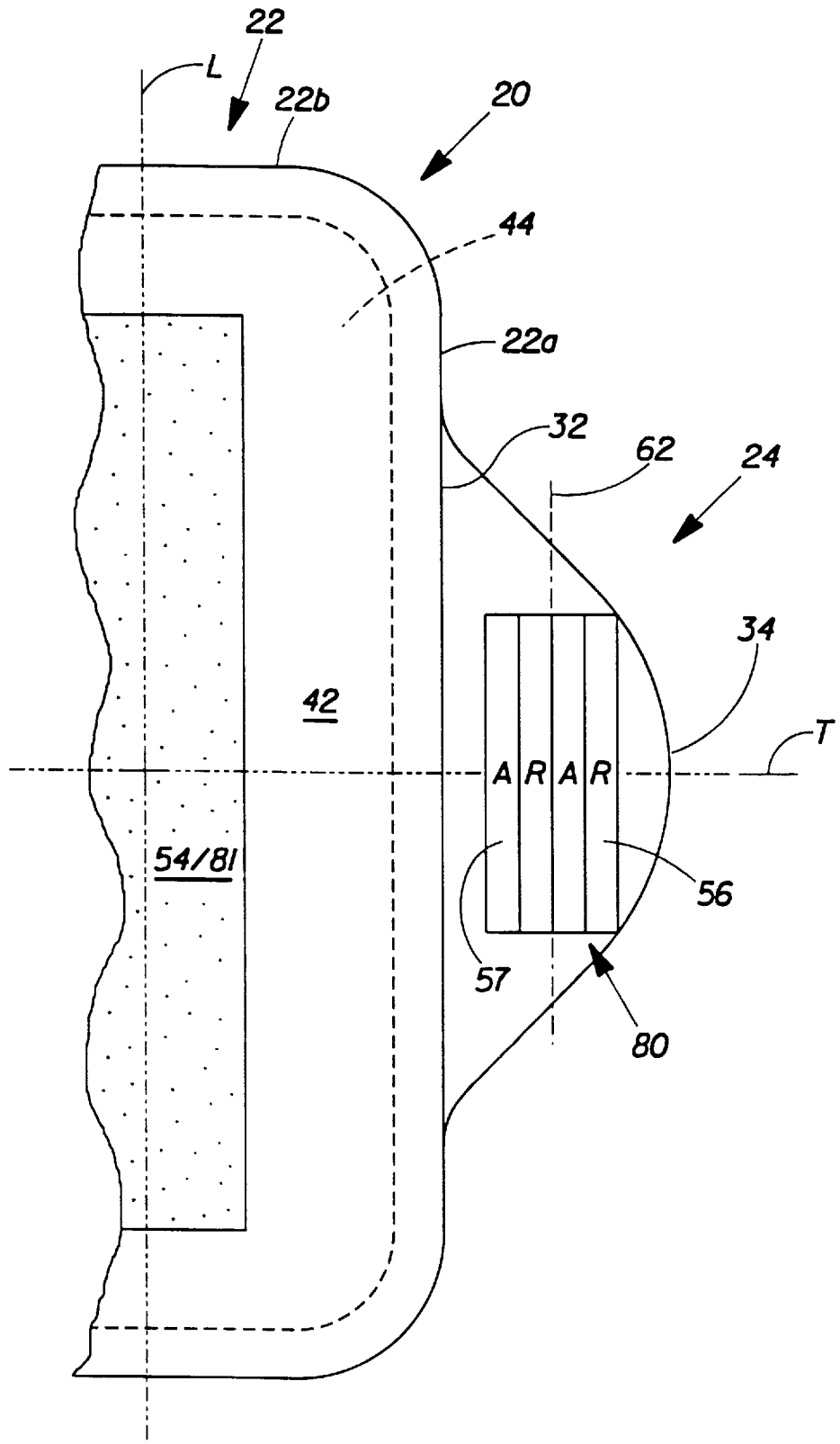
FIG. 5b is a partial top plan view of an alternate sanitary napkin embodiment of the present invention.

FIGS. 5–5b show examples of suitable arrangements for the adhesive zones A and release zones R of the releasable adhesive patch 80. However, it should be understood that these are just examples, and there are many other suitable arrangements which may be used.

D. Function Of The Sanitary Napkin With Relation To The Wearer's Undergarment

The function of the sanitary napkin of the present invention will now be described in greater detail with relation to the wearer's undergarments.

Figure 6:
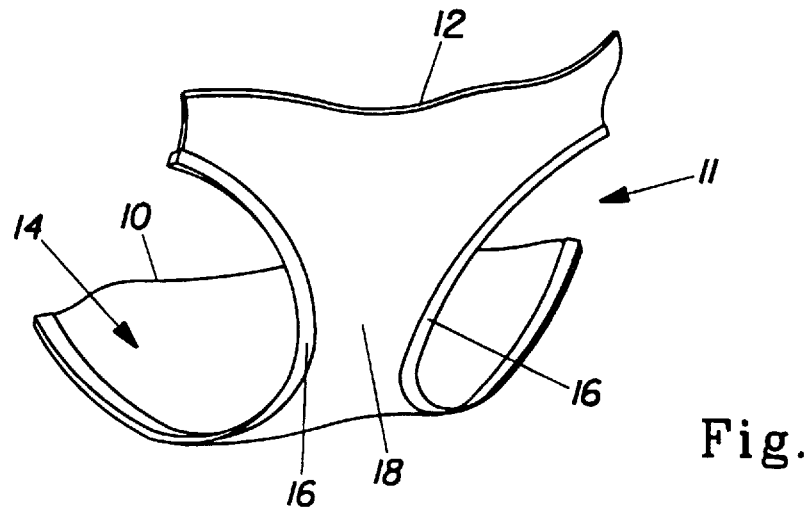
FIG. 6 is a perspective view of the crotch portion of a women's panties.

FIG. 6 is a depiction of the crotch portion 14 of an undergarment 11 of the type commonly worn by many women and well known as a panty. A panty 11 comprises a front section 10, a back section 12, and a crotch portion 14 which joins the front and back sections. The crotch portion 14 comprises two side edges 16 and center crotch portion 18.

Figure 6A:
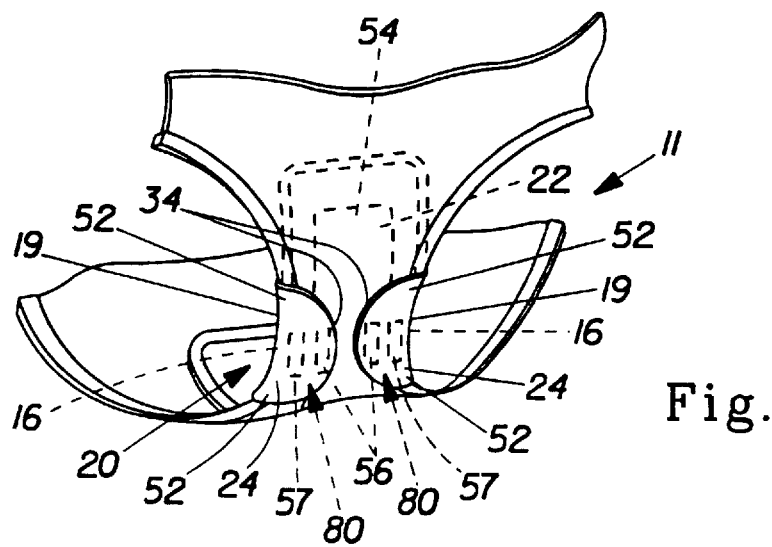
FIG. 6a is the same perspective view of the women's panties shown in FIG. 6 with the sanitary napkin embodiment of the present invention being placed therein for use with the flaps extended and affixed to the underside of the panties.
Figure 6B:
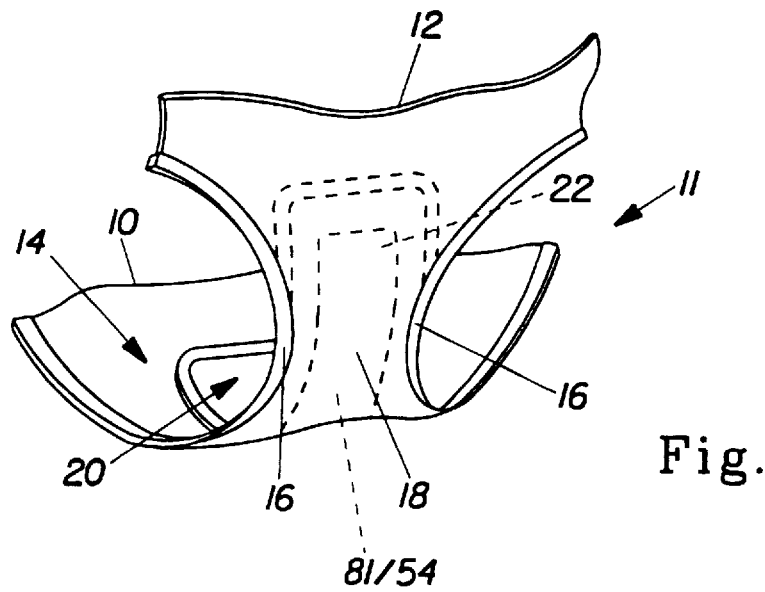
FIG. 6b is the same perspective view of the women's panties shown in FIG. 6 with the a sanitary napkin embodiment of the present invention having tucked flaps, being placed therein for use.

The sanitary napkin 20 of the present invention may be utilized by removing the release liner 58 of the central pad adhesive 54 and placing the sanitary napkin 20 in a panty 11 as shown in FIG. 6b. The center of main body portion 22 is placed in crotch portion 14 of the panty with one end of main body portion 22 extending towards the front section 10 of the panty and the other end towards the back section 12. The backsheet 42 is placed in contact with the inner surface of center crotch portion 18 of the panty. Central pad adhesive 54 maintains main body portion 22 in position. The user grasps and pulls the distal edge 34 of the flap 24, thereby peeling the first half 56 from the second half 57 of the releasable adhesive patch 80. The distal portions of flaps 24 are then folded around the side edges 16 of the panty. The adhesive patches 80 secure the flaps 24 to the underside of the panty as shown in FIG. 6a.

E. Sanitary Napkins Having Tucked Flaps and a Releasable Adhesive Patch

Figure 2:
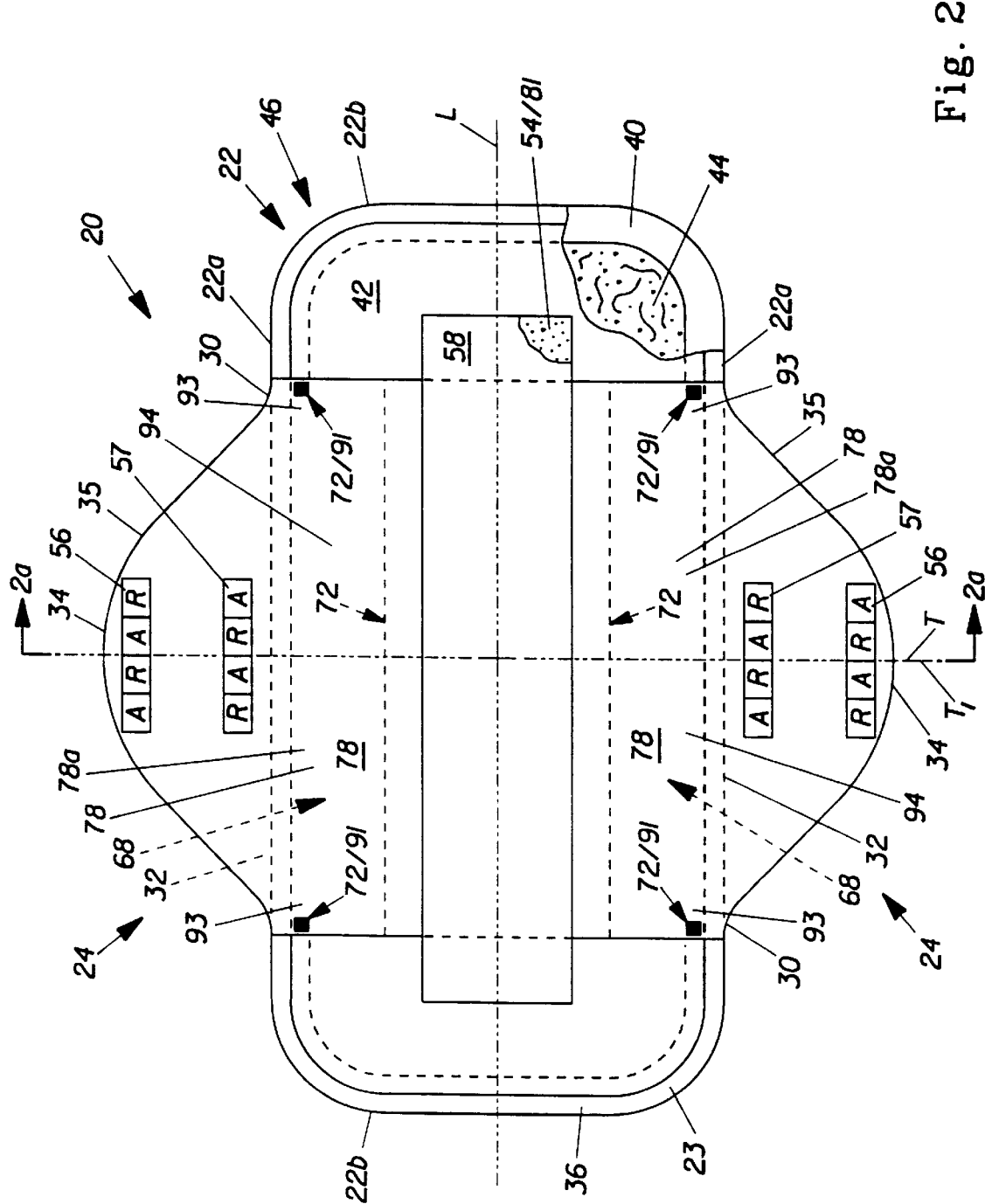
FIG. 2 is a top plan view of an alternate sanitary napkin embodiment of the present invention having portions cutaway to show the absorbent core.
Figure 2A:
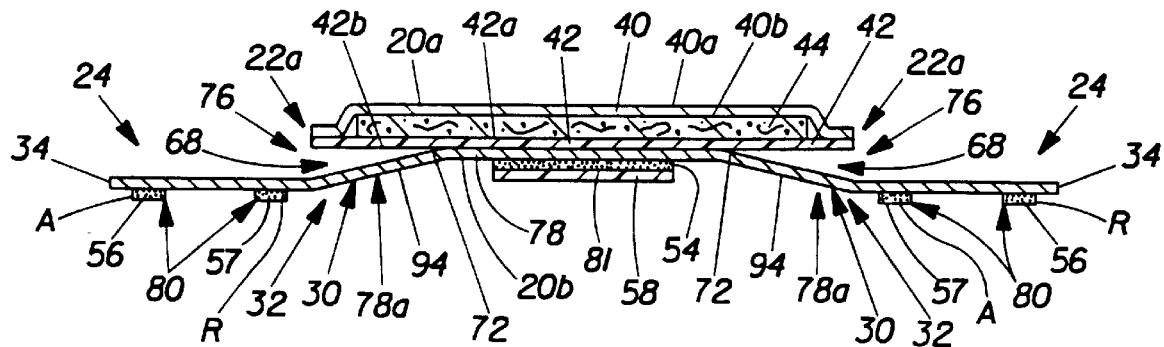
FIG. 2a is a cross-sectional view of the sanitary napkin of FIG. 2 taken along section line a—a.
Figure 2B:
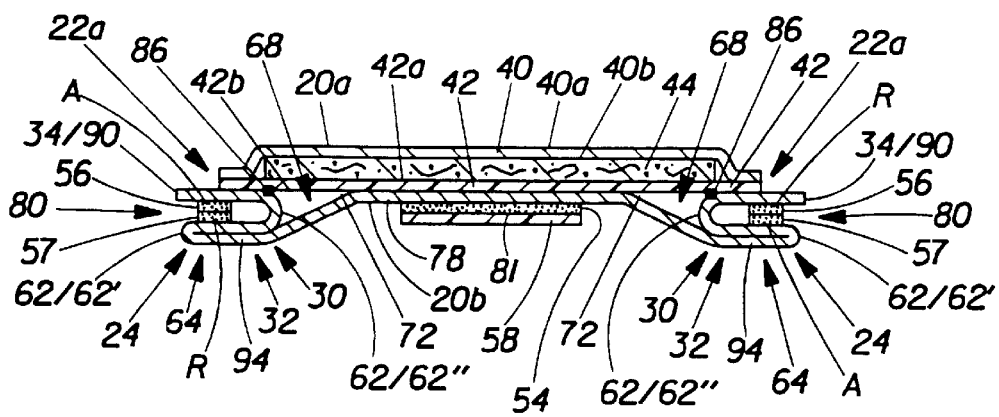
FIG. 2b is a cross-sectional view of the sanitary napkin of FIG. 2a showing the flaps tucked into the recessed areas in a folded configuration.

Preferably, the sanitary napkin will have the flaps tucked into a recessed area and will have at least one zone of differential extensibility. However, it is also possible to have a sanitary napkin of the present invention with the flaps tucked into a recessed area without having zones of differential extensibility. It is also possible to have zones of differential extensibility without having the flaps tucked into a recessed area. FIGS. 2, 2a, and 2b show a sanitary napkin 20 embodiment of the present invention having a releasable adhesive patch 80 and a recessed area 68 for receiving the flaps 24. As used herein the terms "optional flaps" or "tucked flaps" shall refer to the flaps of an absorbent article, which are tucked or are capable of being tucked into a recessed area 68. A flap is capable of being tucked into a recessed area if it is joined to the sanitary napkin such that at least a portion of the flap may be positioned between the decoupled portion of a retaining member and the absorbent assembly of the main body portion. Referring to FIG. 2, the sanitary napkin 20 basically comprises a main body portion 22 and two flaps 24 (shown in the extended position) joined to the main body portion 22. The main body portion 22 comprises an absorbent means represented by an absorbent assembly 46 and two retaining members 78 joined to the absorbent assembly 46.

The retaining member 78 comprises a pair of end regions 93 and a center region 94 positioned between and joined to the end regions 93. At least a portion of the end regions 93 are joined to the absorbent assembly 46. At least a portion of the center region 94 is detached or decoupled from the absorbent assembly 46. The area between the decoupled center region 94 and the absorbent assembly 46, forms a recessed area 68 wherein a portion of at least one of the flaps 24 may be tucked. The end regions 93 are each joined to the absorbent assembly 46 at a point of connection 72. As used herein, the term "point of connection" refers to regions where the retaining member 78 is joined to the absorbent assembly 46 of the main body portion 22. These regions can be of any shape or configuration, but they are not limited to spots or points. Thus, these regions can comprise flanges, strips, intermittent lines, spots, and the like.

The retaining member 78 can be joined to the absorbent assembly 46 of the main body portion 22 in a number of different manners. Many of the different ways a component (such as the retaining member 78) can be "joined to" or "associated with", etc. another component are set forth in the definitions of these terms contained in U.S. Pat. No. 5,007,906 entitled "Decoupled Sanitary Napkin" which issued to Osborn, et al. on Apr. 16, 1991. When the retaining member is comprised of an element discrete from the absorbent assembly 46, i.e. is not integral with the topsheet, backsheet, etc, it can be joined to the absorbent assembly 46 by any techniques known to those skilled in the art. Such techniques include, but are not limited to adhesives, heat and/or pressure, ultrasonics, etc. The point of connection 72 may comprise flanges, strips, intermittent lines, spots, and the like, or may comprise combinations of flanges, strips, intermittent lines, spots, and the like. Therefore, the point of connection 72 may be a line which is concave, straight, or convex and may form any angle relative to the principal longitudinal centerline L.

The retaining member 78 is generally compliant soft feeling and non-irritating to the users skin. The retaining member 78 is preferably made from any of the materials conventionally used for sanitary napkins 20. Examples of suitable materials that can be used for the retaining member 78 are woven and nonwoven polyester, polypropylene, nylon, and polyethylene, as well as plastic films. The retaining member 78 may be comprised of one or more of the elements of the absorbent assembly 46, e.g., topsheet 40, backsheet 42, etc. Preferably, the retaining member 78 will comprise a piece of material discrete from the topsheet, backsheet, etc.

Referring to FIGS. 2–2b, the sanitary napkin 20 has two recessed areas 68, one on each side of the longitudinal centerline L. It can be seen from FIGS. 2a and 2b that the flaps 24 are integral with the retaining members 78. The point of connection 72 of each retaining member 78 comprises a combination of a straight line bond 92 and two spot bonds 91. The line bond 92 joins a portion of the center region 94 of the retaining member 78 to the absorbent assembly 46. The two spot bonds 91 join a portion of the end regions to the absorbent assembly 46. The portion of the center region 94 which is decoupled from the absorbent assembly 46 of the main body portion 22 forms the recessed area 68. Although the spot bonds 91 are shown in FIG. 2 as being positioned adjacent to the longitudinal edge 22a of the main body portion 22, the spot bonds 91 may be positioned anywhere between the longitudinal edge 22a of the main body portion 22 and the longitudinal centerline L.

FIG. 2b is a lateral cross-sectional view of the sanitary napkin 20 of FIG. 2a showing the flaps 24 tucked into the recessed areas 68 in a folded configuration. Each flap 24 of the sanitary napkin 20 has a first longitudinal fold 62' which is made upward toward the absorbent assembly 46 and a second fold 62" which is again made upward toward the absorbent assembly 46. This forms a tucked flap 24 which is configured in an S-fold. This configuration allows the distal edge 34 of the flap 24 to form a graspable tab member 90.

Each of the folded flaps 24 may be provided with one or more breakable bonds 86 which hold the flaps 24 in a folded configuration. Examples of suitable breakable bonds 86 would include adhesive spot beads, spot welds/heat seals, and cohesive materials such as a complementary cohesive adhesive. The breakable bond 86 may secure a portion of the flap 24 to a portion of the main body portion 22 as shown in FIG. 2b. Alternatively, the breakable bond 86 may secure a portion of the flap 24 to another portion of the same flap 24, or to a portion of the retaining member 78.

Preferably each tucked flap 24 will be provided with a graspable tab member 90. As used herein, the term "tab member" will refer to an element or component of the sanitary napkin 20 which protrudes form the recessed area 68 and may be used to remove the flap 24 from the recessed area 68. A preferred tab member 90 is formed by folding, pleating, or corrugating the flap 24 such that the distal edge 34 of the flap 24 protrudes from the mouth 76 of the recessed area 68. There are many different fold configurations which will result in the distal edge 34 of the flap 24 protruding from the mouth 76 of the recessed area 68. An example of particularly preferred fold configurations which results in the distal edge of the flap 24 forming a tab member 90, are shown in FIG. 2b, 3b, and 7a. Other suitable fold configurations will be readily apparent to those skilled in the art.

Sanitary napkins having tucked flaps 24 and various methods for forming the recessed areas 68, are discussed in greater detail in the commonly-assigned, co-pending, U.S. patent application Ser. No. 07/906,629, "Absorbent Article Having Tucked Flaps", filed Jun. 30, 1992, in the name of Thomas W. Osborn, III and Bruce W. Lavash, which patent application is incorporated herein by reference.

F. Sanitary Napkin Having Flaps With Zones of Differential Extensibility and a Releasable Adhesive Patch Preferably, the sanitary napkin will have at least one zone of differential extensibility (or "zone of extensibility", or simply "zone") 50. Preferably, as shown in FIG. 3, the sanitary napkin 20 has four zones of differential extensibility 50, one in each quarter of the sanitary napkin 20. The zones of differential extensibility 50 are preferably located along a portion of the fold line where the flaps 24 are folded around the wearer's panty crotch. The fold line will typically be located along or adjacent the longitudinal juncture 30 of each flap 24. Since the terms "portions", "zones", and "regions", as used herein, refer to general areas, the zones of differential extensibility 50 and the corner regions 52 are, thus, not limited to points which lie precisely on the lines of juncture 30. Typically, they will include both those points which lie on the lines of juncture 30 as well as the surrounding areas of the sanitary napkin 20 (which include the aforementioned fold lines). The longitudinal junctures, thus, typically serve as good approximations for the location of the zones of differential extensibility 50.

Figure 3A:
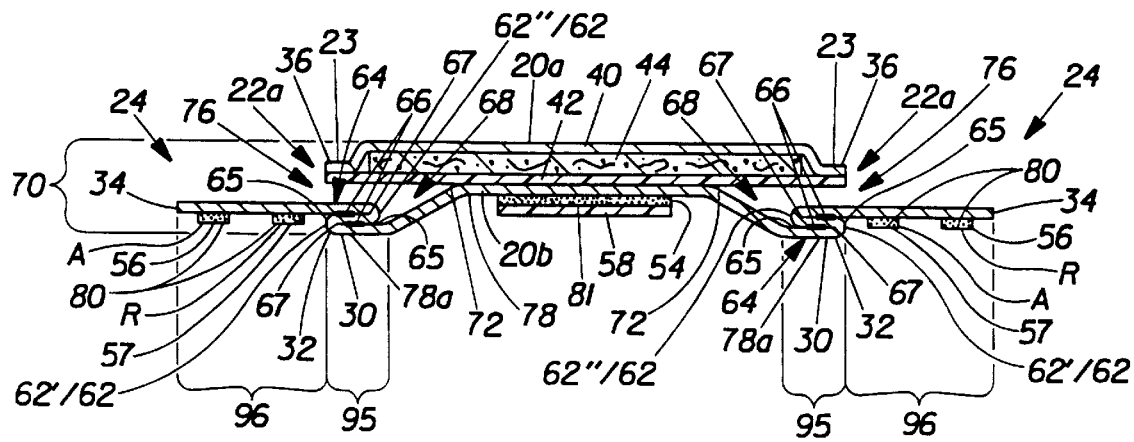
FIG. 3a is a transverse cross-sectional view of the sanitary napkin of FIG. 3.
Figure 3B:
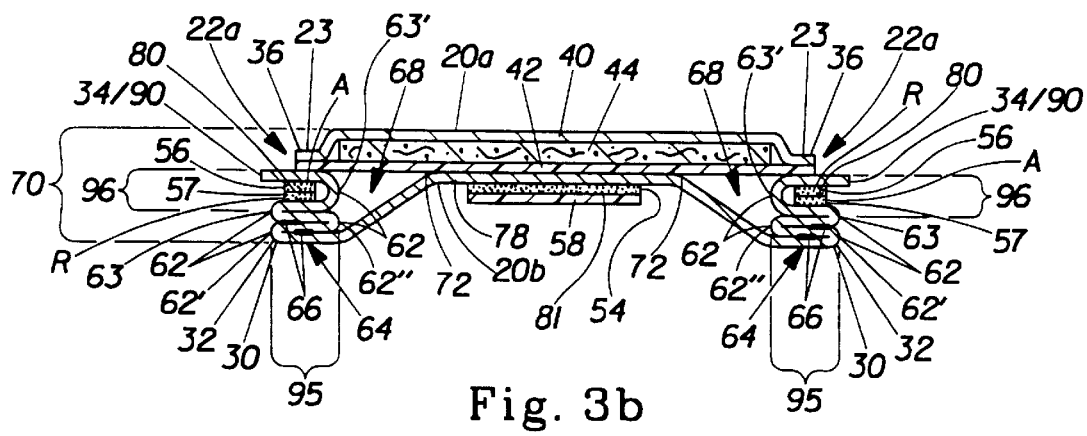
FIG. 3b is a cross-sectional view of the sanitary napkin of FIG. 3 showing the flaps tucked into the recessed areas in a folded configuration.

FIGS. 3, 3a, and 3b show an embodiment of the present invention which has one preferred type of zones of differential extensibility 50. In the embodiment shown in FIGS. 3, 3a, and 3b the zones of differential extensibility 50 comprise portions of the sanitary napkin 20 that have slack provided therein. These portions of the sanitary napkin 20 comprise at least the flap corner regions 52'.

The slack is provided to the sanitary napkin 20 in the embodiment shown in FIGS. 3, 3a, and 3b by pleating and then gathering in portions of the flaps. The flaps 24 are pleated or folded with generally longitudinally-oriented fold lines 62. The fold lines 62 can run along and/or outboard (or even inboard) of the juncture 30 of the flaps and the main body portion 22. The pleated sections of the flaps (the "pleats") 64 are preferably folded on top of each other (that is, stacked perpendicular to the plane of the sanitary napkin). In alternative embodiments, they may be folded and arranged side-by-side. The pleated sections are gathered in or restrained from opening by a flap pleat restraint 66 located along the flap transverse centerline $T_1$. This provides the sanitary napkin, and particularly the flaps 24, with corner regions which are extensible in the transverse direction and with center portions 27 (along the flap transverse centerline $T_1$) which are not.

The zones of differential extensibility 50 are most preferably located at those points where the edges 35 of the flaps 24 intersect the edges 16 of the panty when the sanitary napkin 20 is worn.

The total area covered by the zones of differential extensibility 50 can vary widely. The area can cover a relatively large portion of the sanitary napkin, provided there remain some portions of the sanitary napkin adjacent at least portions of the principal longitudinal centerline and the flap transverse centerline that are less extensible. The zones of differential extensibility 50 can be provided along the entire juncture 30 of the flaps 24 with the main body portion 22. In alternative embodiments, the zones of differential extensibility 50 can be provided throughout the entire flap (for instance, if the entire flap is pleated with longitudinally-oriented pleats).

The flap pleat restraint 66 can be any suitable type of element capable of keeping a portion of the pleated material from unfolding. The flap pleat restraint 66 can be located along the flap transverse centerline $T_1$, or it can be spaced some distance away from the flap transverse centerline $T_1$. The flap pleat restraint 66 is, however, preferably located at some place along the flap transverse centerline $T_1$. This creates flaps with pleats which are able to open up an equal amount in both the front and back halves 26 and 28 for a preferred fit around the panty crotch. The flap pleat restraint 66 is also preferably located more toward the mouth 65 of the fold as opposed to the crease 67 of the fold as shown in FIG. 3. The amount of differential extensibility of the flap will increase as the flap pleat restraint 66 is positioned close to the mouth 65 of the fold. The flaps 24 can have two flap pleat restraints 66, one located along (or spaced some distance away from) the flap transverse centerline $T_1$ for each flap, or they can have a single flap pleat restraint that spans from one flap to the other.

The flap pleat restraints 66 shown in FIG. 3a are "interior" restraints, i.e., they are located in between two pleated or folded sections 64 of the flaps 24. In alternative embodiments, the flap pleat restraint 66 can be of a type which secures the pleated sections 64 of the flaps 24 from outside (or exterior) of the pleated sections.

Referring to FIG. 3a and 3b, each flap 24 of this embodiment has a first portion 95 and a second portion 96. The first portion 95 comprises a pleat 64 which is secured by flap pleat restraints 66. The second portion 96 comprises the first half 56 and the second half 57 of the releasable adhesive patch 80.

The first portion 95 of each flap 24 has two fold lines 62 that form the pleat 64. The first fold that forms the pleat 64 is made inward toward the garment side 20b of the sanitary napkin 20. The second fold that forms the pleat 64 is also made inward towards the garment side 20b of the sanitary napkin 20. The fold line 62 that is closest to the proximal edge 32 of the flap 24 when the first portion 95 is unfolded, comprises a first pleat-forming fold line 62'. The fold line 62 that is located farther away from the proximal edge 32 of the flap 24 when the first portion 95 is unfolded, comprises a second pleat-forming fold line 62".

The pleat 64 of the first portion 95 of the flap 24, is positioned inboard of the longitudinal edge 22a of the main body portion 22 when the sanitary napkin 20 is looked at from a top plan view such as in FIG. 3. This results in the pleat 64 of the first portion 95 being positioned in the recessed area 68 between the retaining member 78 and the backsheet 42 of the main body portion 22 when the flap 24 is extended as shown in FIG. 3a or when the flap is tucked as shown in FIG. 3b.

Again referring to FIGS. 3, 3a, and 3b, the second portion 96 of each flap 24 comprises the first half 56 and the second half 57 of the releasable adhesive patch 80. The first half 56 is positioned adjacent to the distal edge 34 of the flap 24 and the second half 57 is positioned adjacent to the first portion 95 of the flap 24, such that when the second portion 96 is folded along a longitudinally extending fold line 62, the first half 56 will superpose the second half 57 and be removably secured thereto.

Figure 4:
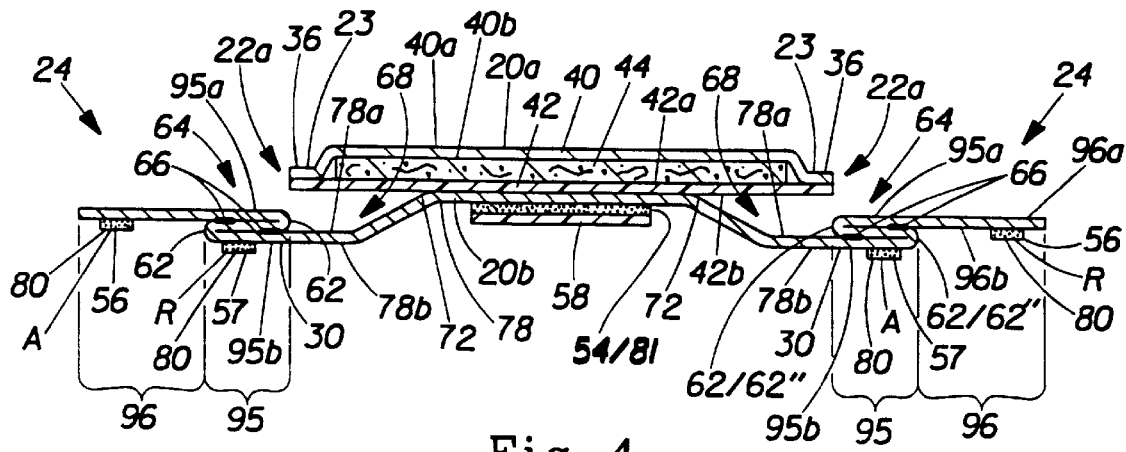
Figure 4A:
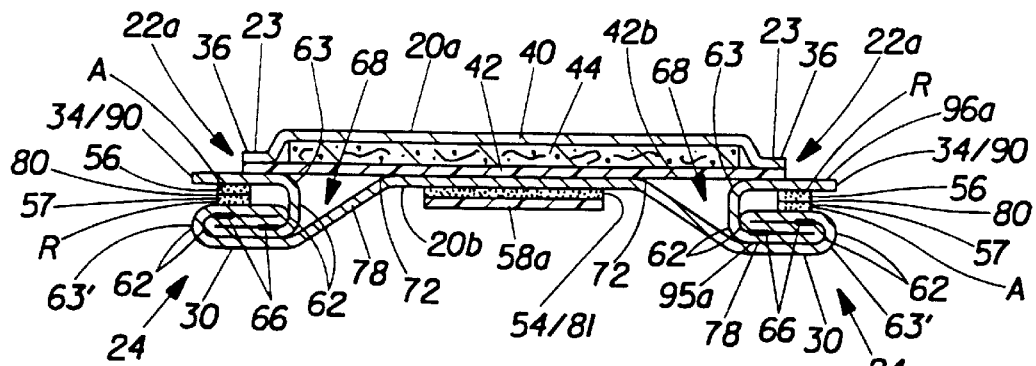
FIG. 4a is a cross-sectional view of the sanitary napkin of FIG. 4 showing the flaps tucked into the recessed areas in a folded and rolled configuration.

A transverse, cross-sectional view of a particularly preferred sanitary napkin embodiment of the present invention, is shown in FIG. 4 and 4a. The embodiment shown in FIGS. 4 and 4a is similar to the embodiment shown in FIGS. 3–3b, i.e., the flaps 24 are extensions of the retaining member 78 which is joined to the backsheet 42 of the main body portion 22 along the lines of connection 72. However, the flaps 24 are arranged in a different configuration when they are tucked, as shown in FIG. 4a, and when they are extended, as shown in FIG. 4.

Referring to FIG. 4, each flap 24 may again be thought of as having a first portion 95 and a second portion 96. The first portion 95 of the flap 24 comprises a pleat 64 which is secured by the flap pleat restraints 66, and comprises the second half of the releasable adhesive patch 80 joined to the body-facing side 95b of the first portion 95. The second portion 96 comprises the first half 56 joined to the garment-facing side 96b of the second portion 96.

The pleat 64 of the first portion 95 of the flap 24, has two longitudinally extending fold lines 62. The fold line that is closest to the proximal edge 32 of the flap 24 when the first portion 95 is unfolded, comprises a first pleat-forming fold line 62'. The fold line 62 that is located farther away from the proximal edge 32 of the flap 24 when the first portion 95 is unfolded, comprises a second pleat-forming fold line 62". The first pleat-forming fold line 62' is formed by folding the flap material toward the garment-facing side 42b of the backsheet 42. The second pleat-forming fold line 62" is also formed by folding the flap material towards the garment-facing side 42b of the backsheet 42. The pleat 64 of the first portion 95 is secured by flap pleat restraints 66 which are located substantially adjacent the mouth of each fold. The first portion 95 of the flap 24 also comprises the second half 57 which is joined to the garment-facing side 95b of the first portion 95.

The first portion 95 of the flap 24 is positioned outboard of the longitudinal edge 22a of the main body portion 22 when the sanitary napkin 20 is looked at from a top plan view. This results in the first portion 95 being positioned outside of the recessed area 68 when the flap 24 is extended as shown in FIG. 4. The second portion 96 of each flap 24 comprises the first half 56 of the releasable adhesive patch 80. The first half 56 is positioned substantially adjacent to the distal edge 34 of the flap 24 and is positioned on the garment-facing side 96b of the second portion 96.

When the flap 24 is tucked into the recessed area 68 as shown in FIG. 4a, the second portion 96 will be folded along a first tuck-forming fold line 63 such that the first half 56 superposes the second half 57 of the releasable adhesive patch 80. The first portion 95 and the second portion 96 are then folded toward the garment-facing side 42b of the backsheet 42 to form a second tuck-forming fold line 63' prime. As shown in FIG. 4a, this results in the body-facing side 95a of the first portion 95 being in substantially face to face relation with the body-facing side 78a of the retaining member 78, and the body-facing side 96a of the second portion 96 being in substantially face to face relation with the garment side 42b of the backsheet 42. Accordingly, this results in the first portion 95 and second portion 96 of the flap 24, being positioned in the recessed area 68 between the retaining member 78 and the backsheet 42 of the sanitary napkin 20. Preferably, as shown in FIG. 4a, when the flap 24 is tucked into the recessed area 68, the distal edge 34 of the flap 24 will form a graspable tap member 90.

Other methods of providing zones of differential extensibility, are discussed in greater detail in commonly-assigned, co-pending, U.S. patent application Ser. No. 07/769,891, "Absorbent Article Having Flaps and Zones of Differential Extensibility", filed Oct. 1, 1991, in the name of Bruce W. Lavash, et al., and in commonly-assigned, co-pending, U.S. patent application Ser. No. 07/832,246, "Absorbent Article Having Inwardly-Folded Pleated Flaps", filed Feb. 7, 1992, in the name of Kaoru Niihara and Thomas W. Osborn, III, which patent applications are incorporated herein by reference.

Thus, the present invention provides a sanitary napkin having flaps with a releasable adhesive patch comprising a first half and a second half which overlies the first half when the flap is folded along a fold line.

While particular embodiments of the present invention have been illustrated and described, it would be obvious to those skilled in the art that various other changes and modifications can be made without departing from the spirit and scope of the invention.

What is claimed is:

1. An absorbent article for wearing in a wearer's undergarment which undergarment has a crotch, said absorbent article having a garment side, a body-facing side, and at least one flap for folding under the crotch portion of said undergarment and fastened, said absorbent article comprising:

a main body portion comprising an absorbent assembly and a longitudinal centerline which divides said main body portion into a first longitudinal half and a second longitudinal half;

a first flap joined to the first longitudinal half of said main body portion at a line of juncture, said first flap comprising a proximal edge substantially adjacent the line of juncture, a distal edge disposed away from the line of juncture, and an adhesive patch joined thereto, said adhesive patch comprising a first half and a second half, said first half comprising adhesive zones and release zones and said second half comprising adhesive zones and release zones which are arranged such that the adhesive zones of said first half are removably secured to at least a portion of the release zones of said second half and the adhesive zones of said second half are removably secured to at least a portion of the release zones of said first half wherein said first flap is provided with an adhesive fastening surface that comprises portions of both said first and second halves of said adhesive patch.

2. The absorbent article of claim 1 wherein said main body portion comprises a pad securement member joined thereto.

3. The absorbent article of claim 2 wherein said pad securement member comprises an adhesive.

4. The absorbent article of claim 1 wherein said second half of said adhesive patch of said first flap is hingedly joined to said absorbent article.

5. The absorbent article of claim 1 wherein said absorbent article comprises a pair of flaps, said first flap and a second flap, said second flap being joined to the second longitudinal half of said main body portion at a line of juncture and comprising a proximal edge substantially adjacent the line of juncture, a distal edge disposed away from the line of juncture, and an adhesive patch joined thereto, said adhesive patch comprising a first half and a second half, said first half comprising adhesive zones and release zones and said second half comprising adhesive zones and release zones which are arranged such that the adhesive zones of said first half are removably secured to at least a portion of the release zones of said second half and the adhesive zones of said second half are removably secured to at least a portion of the the release zones of said first half.

6. The absorbent article of claim 5 wherein said first flap and said second flap each comprise a fold line which is parallel to said principal longitudinal centerline, and is positioned between said first half and said second half of said adhesive patch of each of said flaps.

7. The absorbent article of claim 6 wherein said adhesive zones and said release zones of said adhesive patch of each of said flaps are arranged in alternating strips which are oriented parallel to said fold line.

8. The absorbent article of claim 6 wherein said adhesive zones and said release zones of said adhesive patch of each of said flaps are arranged in alternating strips which are oriented perpendicular to said fold line.

9. The absorbent article of claim 6 wherein said adhesive zones and said release zones of said adhesive patch of each of said flaps are arranged in alternating strips which are oriented at an angle of between 1° and 90° relative to said fold line such that said adhesive patch is configured in a herringbone pattern.

10. The absorbent article of claim 5 wherein said first flap and said second flap each comprise a fold line which is perpendicular to said principal longitudinal centerline, and is positioned between said first half and said second half of said adhesive patch of each of said flaps.

11. The absorbent article of claim 5 wherein each of said flaps is provided with at least one zone of differential extensibility which is extensible outward generally in a transverse direction.

12. The absorbent article of claim 5 wherein said main body portion comprises a pad securement member joined thereto.

13. The absorbent article of claim 12 wherein said pad securement member comprises an adhesive.

14. An absorbent article for wearing in a wearer's undergarment, which undergarment has a crotch prtion, said absorbent article having a garment side and a body-facing side, said absorbent article comprising:

a main body portion comprising an absorbent assembly and a longitudinal centerline which divides said main body portion into a first longitudinal half and a second longitudinal half, a pair of flaps for folding under the crotch portion of said undergarment and fastened, said flaps comprising a first flap joined to the first longitudinal half of said main body portion at a line of juncture and a second flap joined to the second longitudinal half of said main body portion at a line of juncture, each of said flaps comprising a proximal edge substantially adjacent the line of juncture, a distal edge disposed away from the line of juncture, and an adhesive patch joined thereto, said adhesive patch comprising a first half and a second half, said first half comprising adhesive zones and release zones and said second half comprising adhesive zones and release zones which are arranged such that the adhesive zones of said first half are removably secured to at least a portion of the release zones of said second half and the adhesive zones of said second half are removably secured to at least a portion of the release zones of said first half wherein said first flap is provided with an adhesive fastening surface that comprises portions of both said first and second halves of said adhesive patch; and at least one retaining member, said retaining member comprising two end regions, a center region positioned between and joined to said end regions, and a longitudinal edge, at least a portion of each of said end regions being joined to said absorbent assembly at a point of connection, at least a portion of said center region being decoupled from said absorbent assembly to form a recessed area between said center region of said retaining member and said absorbent assembly wherein at least a portion of one of said flaps is capable of being tucked.

15. The absorbent article of claim 14 wherein said main body portion comprises two retaining members joined to said absorbent assembly to form two recessed areas, a first recessed area and a second recessed area wherein said flaps are capable of being tucked.

16. The absorbent article of claim 15 wherein a portion of said first flap is tucked into said first recessed area to form a first tucked flap and a portion of said second flap is tucked into said second recessed area to form a second tucked flap.

17. The absorbent article of claim 16 wherein said first tucked flap comprises a breakable bond which removably secures said second tucked flap to said absorbent article and holds said first tucked flap in said first recessed area and said second tucked flap comprises a breakable bond which removably secures said second tucked flap to said absorbent article and holds said second tucked flap in said second recessed area.

18. The absorbent article of claim 14 wherein said retaining member comprises a discrete piece of material joined to said main body portion.

19. The absorbent article of claim 5 or 14 wherein said second half of said adhesive patch of each of said flaps is hingedly joined to said absorbent article.

20. The absorbent article of claim 19 wherein said second half is joined to said garment side of said flap.

21. The absorbent article of claim 20 wherein said absorbent article additionally comprises a bonding material joined thereto such that said second half may be secured away from said first half when said second half of said adhesive patch has been removed from said first half of said adhesive patch.

22. The absorbent article of claim 19 wherein said second half is joined to said garment side of said main body portion.

23. The absorbent article of claim 22 wherein said absorbent article additionally comprises a bonding material joined thereto such that said second half may be secured away from said first half when said second half of said adhesive patch has been removed from said first half of said adhesive patch.

* * * * *